United States Patent
Huang et al.

(10) Patent No.: US 12,421,260 B2
(45) Date of Patent: **\*Sep. 23, 2025**

(54) NEUROKININ-1 ANTAGONIST

(71) Applicants: SHANGHAI SHENGDI PHARMACEUTICAL CO., LTD, Shanghai (CN); SHANGHAI SENHUI MEDICINE CO., LTD., Shanghai (CN); JIANGSU HENGRUI MEDICINE CO., LTD., Lianyungang (CN)

(72) Inventors: Jian Huang, Shanghai (CN); Lingjian Zhu, Shanghai (CN); Yang Zou, Shanghai (CN); Yinggang Tang, Shanghai (CN)

(73) Assignees: SHANGHAI SHENGDI PHARMACEUTICAL CO., LTD, Shanghai (CN); SHANGHAI SENHUI MEDICINE CO., LTD., Shanghai (CN); JIANGSU HENGRUI MEDICINE CO., LTD., Lianyungang (CN)

( * ) Notice: Subject to any disclaimer, the term of this patent is extended or adjusted under 35 U.S.C. 154(b) by 939 days.

This patent is subject to a terminal disclaimer.

(21) Appl. No.: 17/623,205

(22) PCT Filed: Jun. 28, 2020

(86) PCT No.: PCT/CN2020/098460
§ 371 (c)(1),
(2) Date: Dec. 27, 2021

(87) PCT Pub. No.: WO2020/259675
PCT Pub. Date: Dec. 30, 2020

(65) Prior Publication Data
US 2022/0380393 A1  Dec. 1, 2022

(30) Foreign Application Priority Data

Jun. 28, 2019 (CN) ........................ 201910572272.1
Dec. 27, 2019 (CN) ........................ 201911375262.5

(51) Int. Cl.
*C07D 471/10* (2006.01)
*C07D 471/04* (2006.01)
*C07F 9/09* (2006.01)

(52) U.S. Cl.
CPC .............. *C07F 9/09* (2013.01); *C07D 471/04* (2013.01)

(58) Field of Classification Search
CPC .................................................. C07D 471/10
See application file for complete search history.

(56) References Cited

U.S. PATENT DOCUMENTS

| 5,620,989 | A | 4/1997 | Harrison et al. |
| 5,760,018 | A | 6/1998 | Baker et al. |
| 7,049,320 | B2 | 5/2006 | Paliwal et al. |
| 9,101,615 | B2 | 8/2015 | Wan et al. |
| 2016/0024092 | A1* | 1/2016 | Wan ........................ A61P 25/24 546/16 |

FOREIGN PATENT DOCUMENTS

| CN | 1897942 A | 1/2007 | |
| CN | 102573475 A | 7/2012 | |
| WO | 94/10165 A1 | 5/1994 | |
| WO | 94/13639 A1 | 6/1994 | |
| WO | 95/19344 A1 | 7/1995 | |
| WO | WO-9822542 A2 * | 5/1998 | ................ C08J 5/06 |

OTHER PUBLICATIONS

Xiujuan Wu et al., Stereoselective Transformation of 2H-1,4-Oxazin-2-ones into 2,(2),5,5-Tri-and Tetrasubstituted Analogues of cis-5-Hydroxy-2-piperidinemethanol and cis-5-Hydroxy-6-oxo-2-piperidinecarboxylic Acid, Tetrahedron Letters 56, Mar. 2, 2000, pp. 3043-3051, Elsevier Science Ltd., Belgium (9 pages).

(Continued)

*Primary Examiner* — Matthew P Coughlin
(74) *Attorney, Agent, or Firm* — Morgan, Lewis & Bockius LLP

(57) ABSTRACT

A compound represented by formula II or a pharmaceutically acceptable salt thereof, and a preparation method therefor. The compound represented by formula II is an antagonist of a neurokinin-1 receptor, can be used for treating diseases related to the neurokinin-1 receptor, and can avoid hemolytic effects of drugs and reduce the side effects of drug administration.

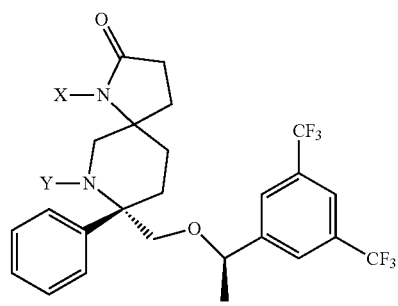

7 Claims, 1 Drawing Sheet

(56) References Cited

OTHER PUBLICATIONS

Joeri Rogiers et al., Stereoselective conversion of 2H-1,4-oxazin-2ones into 2,5,5-substituted piperidine-2-carboxamides and 2-methanamines and related octahydro-2H-pyrido[1,2-a]pyrazines, potential substance P antagonists, Tetrahedron Letters 57, Sep. 4, 2001, pp. 8971-8981, Elsevier Science Ltd., Belgium (11 pages).

Frederik J. R. Rombouts et al., Intramolecular Diels—Alder reactions of N-alkenyl-2(1H)-pyrazinones: generation of a novel type of cis-1,7-naphthyridine, Tetrahedron Letters 42, Aug. 23, 2001, pp. 7397-7399, Elsevier Science Ltd., Belgium (3 pages).

* cited by examiner

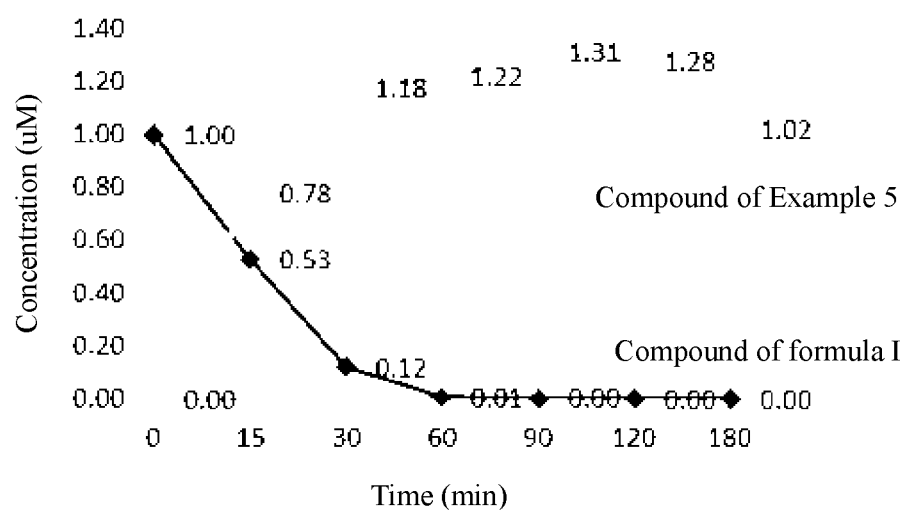

NEUROKININ-1 ANTAGONIST

CROSS-REFERENCE TO RELATED APPLICATIONS

The present application is the national stage of International Patent Application No. PCT/CN2020/098460, filed on Jun. 28, 2020, which claims the benefit of and priority to Chinese Patent Application No. 201910572272.1 filed on Jun. 28, 2019, and Chinese Patent Application No. CN201911375262.5 filed on Dec. 27, 2019.

TECHNICAL FIELD

The present disclosure relates to an antagonist of the neuropeptide neurokinin-1 (NK1 or NK-1) receptor.

BACKGROUND

Tachykinin is a peptide ligand for neurokinin receptors. Neurokinin receptors, such as NK1, NK2 and NK3, are involved in various biological processes. They can be found in the nervous and circulatory system and in surrounding tissues of mammals. Therefore, the modulation of such receptors has been studied for potential treatment or prevention of various diseases in mammals. Typical neurokinin receptor antagonists and their uses include: U.S. Pat. No. 5,760,018 (1998) (pain, inflammation, migraine and vomiting), U.S. Pat. No. 5,620,989 (1997) (pain, nociception and inflammation), WO95/19344 (1995), WO 94/13639 (1994) and WO 94/10165 (1994). Other types of NK1 receptor antagonists include: Wu et al., *Tetrahedron* 56, 3043-3051 (2000); Rombouts et al., *Tetrahedron Letters* 42, 7397-7399 (2001); and Rogiers et al., *Tetrahedron* 57, 8971-8981 (2001).

U.S. Pat. No. 7,049,320 provides an effective and selective NK1 antagonist, (5S,8S)-8-[{(1R)-1-(3,5-bis-(trifluoromethyl)phenyl)-ethoxy}-methyl]-8-phenyl-1,7-diazaspiro[4.5]dec-2-one (compound of formula I) with beneficial therapeutic and pharmacological properties and good metabolic stability, which can be in the form of a free base or a pharmaceutically acceptable salt, and is suitable for a preparation for parenteral administration,

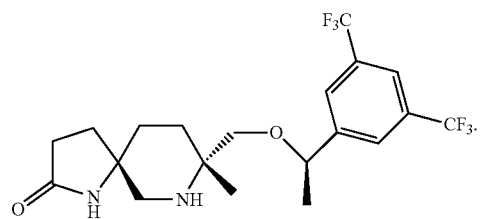

I

U.S. Pat. No. 9,101,615 provides a prodrug of the compound of formula I, that is, a prodrug and a salt thereof in which the free amine (or two amines) of the compound of formula I is replaced by a group selected from —Y and —X, wherein Y is selected from the group consisting of —P(O)(OH)$_2$, —S(O)$_{n1}$R$^1$, —C(O)(C$_{1-6}$ alkyl)X, —C(O)(C$_{1-6}$ alkyl)(aryl) and —C(O)OR$^4$; X is selected from the group consisting of —NR$^2$R$^3$, —P(O)(OH)$_2$ and —S(O)$_{n1}$R$^1$; R$^1$ is H or C$_{1-6}$ alkyl; R$^2$ is H or C$_{1-6}$ alkyl; R$^3$ is H or C$_{1-6}$ alkyl; R$^4$ is H or C$_{1-6}$ alkyl; n1 is 0-4. The prodrug can be used in a suitable liquid formulation (including or excluding the parenteral carrier for delivery) to treat patients in need thereof.

In another aspect, drug-induced hemolysis is resulted from the massive destruction of erythrocytes caused by immune factors after the drug enters the human body. Clinically appeared hemolysis symptoms are anemia, jaundice, soy sauce-like urine and the like. Drug-induced hemolytic anemia can be classified into the following three types: (1) drug-induced immunity, leading to antibody-mediated hemolytic reactions; (2) action of drug on erythrocytes with genetic enzyme deficiency (for example G6PD deficiency); (3) drug-induced hemolytic reaction to abnormal hemoglobin. The key to treating such diseases is to stop using related drugs and to control the occurrence of hemolysis in order to prevent the occurrence of complications. In order to solve the problem of the low solubility of the compound of formula I at physiological pH, researchers have used a co-solvent-based formulation containing Captisol, propylene glycol and ethanol to significantly improve the solubility of compound 1, but the co-solvent-based formulation has significant hemolytic effect after intravenous administration. CN102573475 discloses an improved formula containing polyethylene glycol 15-hydroxystearate and medium chain triglycerides. However, even if the compound of formula I is prepared as a prodrug containing phosphates, the hemolytic effect of the pharmaceutical composition is still not completely resolved.

The present application provides a new NK1 antagonist prodrug compound that is effective in treating various physiological disorders, conditions and diseases and has minimal side effects.

SUMMARY OF THE INVENTION

The present disclosure provides a compound of formula II:

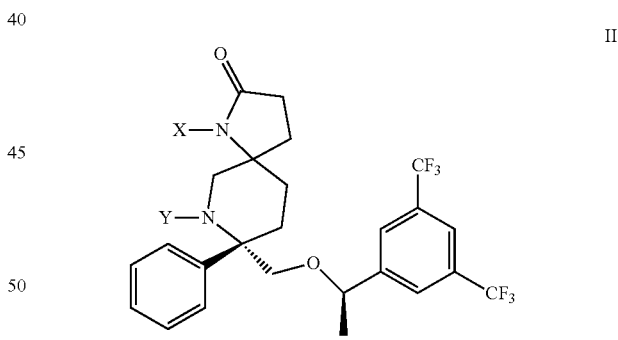

II or a pharmaceutically acceptable salt thereof, or a stereoisomer, rotamer or tautomer thereof, or a deuteride thereof,
wherein, X is selected from the group consisting of hydrogen, heterocyclyl, aryl, heteroaryl, —C(O)OA$_m$R$^3$, —C(O)NR$^4$A$_m$R$^3$, -A$_m$[C(R$^1$)(R$^2$)]C(O)OA$_n$R$^3$, -A$_m$OC(O)[C(R$^1$)(R$^2$)]A$_n$R$^3$, -A$_m$C(O)NR$^4$A$_n$R$^3$, -A$_m$NR$^4$C(O)A$_n$R$^3$ and -A$_m$R$^5$, said heterocyclyl, aryl or heteroaryl is optionally substituted by one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R"), COOR' and CONR'(R");
Y is selected from the group consisting of hydrogen, —C(O)OA$_m$R$^3$, —C(O)NR$^4$A$_m$R$^3$, -A$_m$[C(R$^1$)(R$^2$)]C (O)OA$_n$R$^3$, -A$_m$OC(O) [C(R$^1$)(R$^2$)]A$_n$R$^3$, -A$_m$C(O)NR$^4$A$_n$R$^3$, -A$_m$NR$^4$C(O)A$_n$R$^3$ and -A$_m$R$^5$;

A is independently selected from the group consisting of —C(R$^1$)(R$^2$)(B)$_p$— and —(B)$_q$C(R$^1$)(R$^2$)—, R$^1$, R$^2$ and R$^4$ are each independently selected from the group consisting of hydrogen, alkyl, cycloalkyl, heterocyclyl, aryl and heteroaryl, said alkyl, cycloalkyl, heterocyclyl, aryl or heteroaryl is optionally substituted with one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R"), COOR' and CONR'(R");

R$^3$ is selected from the group consisting of hydrogen, alkyl, cycloalkyl, heterocyclyl, aryl, heteroaryl, poly(oxyethyleneoxy)

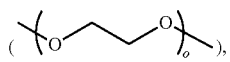

poly(ethyleneoxy)

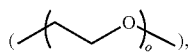

OPO(R$^6$)$_2$, PO(R$^6$)$_2$, OSO$_2$(R$^6$)$_2$, SO$_2$(R$^6$)$_2$, OC(O)R$^6$ and C(O)OR$^6$, said alkyl, cycloalkyl, heterocyclyl, aryl or heteroaryl is optionally substituted with one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R"), COOR' and CONR'(R");

R$^5$ is selected from the group consisting of heterocyclyl, heteroaryl, OSO$_2$R$^7$, OC(O)R$^7$, SR',

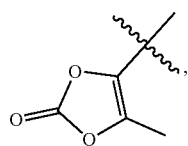 [SMILES: *c1oc(=O)oc1C]

SO$_2$R' and NR'(R");

each of R$^6$ is independently selected from the group consisting of hydrogen, hydroxyl, alkyl, cycloalkyl, heterocyclyl, aryl, heteroaryl, alkoxyl, hydroxyalkyl and NR'(R"), said alkyl, hydroxyalkyl, cycloalkyl, heterocyclyl, aryl or heteroaryl is optionally substituted with one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R"), COOR' and CONR'(R");

each of R$^7$ is independently selected from the group consisting of alkyl, hydroxyl, cycloalkyl, heterocyclyl, aryl, heteroaryl, hydroxyalkyl and NR'(R"), said alkyl, hydroxyalkyl, cycloalkyl, heterocyclyl, aryl or heteroaryl is optionally substituted with one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R"), COOR' and CONR'(R");

R' and R" are each independently selected from the group consisting of hydrogen, hydroxyl, alkyl (preferably selected from the group consisting of C$_{1-12}$ alkyl, including but not limited to methyl, ethyl or isopropyl), alkoxyl (preferably selected from the group consisting of C$_{1-12}$ alkoxyl), alkenyl and acyl;

B is each independently selected from the group consisting of O, N and SC(O);

m, n and o are each independently selected from the group consisting of 1~10, and can be 1, 2, 3, 4, 5, 6, 7, 8, 9 or 10;

p and q are each independently selected from the group consisting of 0 and 1; and, X and Y are not hydrogen at the same time.

The compound of formula II of the present disclosure has better solubility than that of the parent drug, the compound of formula I, and is thus suitable for intravenous administration. In addition, the compound as described above will be degraded and release the parent drug under physiological conditions when entering into the human body after formulated into an intravenous preparation, which will delay the release of the drug, and prolong the release period of the drug.

In an alternative embodiment of the present disclosure, in the compound of formula II, X is selected from the group consisting of hydrogen, heterocyclyl, aryl, heteroaryl, —C(O)O[C(R$^1$)(R$^2$)(O)$_p$]$_m$R$^3$, —C(O)NR$^4$[C(R$^1$)(R$^2$)(O)$_p$]$_m$ R$^3$, —[C(R$^1$)(R$^2$)(O)$_p$]$_m$C(O)[C(R$^1$)(R$^2$)(O)$_p$]$_n$R$^3$, —[C(R$^1$)(R$^2$)(O)$_p$]$_m$[C(R$^1$)(R$^2$)]C(O)[(O)$_q$C(R$^1$)(R$^2$)]$_n$R$^3$, —[C(R$^1$)(R$^2$)(O)$_p$]$_m$C(O)NR$^4$[C(R$^1$)(R$^2$)(O)$_p$]$_n$R$^3$ and —[C(R$^1$)(R$^2$)(O)$_p$]$_m$R$^5$, said alkyl, cycloalkyl, heterocyclyl, aryl or heteroaryl is optionally substituted with one or more groups selected from the group consisting of alkyl (preferably selected from C$_{1-12}$ alkyl, including but not limited to methyl, ethyl or isopropyl), cycloalkyl (preferably selected from C$_{1-12}$ cycloalkyl, such as cyclohexyl and cyclopentanyl), alkoxyl (preferably selected from C$_{1-12}$ alkoxyl), hydroxyalkyl, alkenyl, alkynyl, aryl, heteroaryl, nitro, cyano, hydroxyl, halogen, SR', NR'(R"), COOR' and CONR'(R");

Y is selected from the group consisting of hydrogen, —C(O)O[C(R$^1$)(R$^2$)(O)$_p$]$_m$R$^3$, —C(O)NR$^4$[C(R$^1$)(R$^2$)(O)$_p$]$_m$ R$^3$, —[C(R$^1$)(R$^2$)(O)$_p$]$_m$C(O)[C(R$^1$)(R$^2$)(O)$_p$]$_n$R$^3$, —[C(R$^1$)(R$^2$)(O)$_p$]$_m$C(O)[(O)$_q$C(R$^1$)(R$^2$)]$_n$R$^3$, —[C(R$^1$)(R$^2$)(O)$_p$]$_m$C(O)NR$^4$[C(R$^1$)(R$^2$)(O)$_p$]$_n$R$^3$ and —[C(R$^1$)(R$^2$)(O)$_p$]$_m$R$^5$, and X and Y are not hydrogen at the same time.

In an alternative embodiment of the present disclosure, in the compound of formula II, Y is selected from the group consisting of —C(O)O[C(R$^1$)(R$^2$)]$_m$R$^3$, —C(O)NR$^4$[C(R$^1$)(R$^2$)]$_m$R$^3$, —[C(R$^1$)(R$^2$)O]$_m$C(O)[C(R$^1$)(R$^2$)]$_n$R$^3$, —[C(R$^1$)(R$^2$)]$_m$C(O) [OC(R$^1$)(R$^2$)]$_n$R$^3$, —[C(R$^1$)(R$^2$)N]$_m$C(O)[C(R$^1$)(R$^2$)]$_n$R$^3$, [C(R$^1$)(R$^2$)N]$_m$C(O)[OC(R$^1$)(R$^2$)]$_n$R$^3$, [C(R$^1$)(R$^2$)N]$_m$C(O)[NC(R$^1$)(R$^2$)]$_n$R$^3$, —[C(R$^1$)(R$^2$)(O)$_p$]$_m$C(O)NR$^4$[C(R$^1$)(R$^2$)(O)$_p$]$_n$R$^3$ and —[C(R$^1$)(R$^2$)(O)$_p$]$_n$R$^5$, X is hydrogen or 3 to 6 membered heterocyclyl.

In an alternative embodiment of the present disclosure, in the compound of formula II, Y is selected from the group consisting of —C(O)O[C(R$^1$)(R$^2$)]$_m$R$^3$, —C(O)NR$^4$[C(R$^1$)(R$^2$)]$_m$R$^3$, —[C(R$^1$)(R$^2$)O]$_m$C(O)[C(R$^1$)(R$^2$)]$_n$R$^3$, —[C(R$^1$)(R$^2$)]$_m$C(O)[OC(R$^1$)(R$^2$)]$_n$R$^3$, —[C(R$^1$)(R$^2$)N]$_m$C(O)[C(R$^1$)(R$^2$)]$_n$R$^3$, [C(R$^1$)(R$^2$)N]$_m$C(O)[OC(R$^1$)(R$^2$)]$_n$R$^3$, [C(R$^1$)(R$^2$)N]$_m$C(O)[NC(R$^1$)(R$^2$)]$_n$R$^3$, —[C(R$^1$)(R$^2$)(O)$_p$]$_m$C(O)NR$^4$[C(R$^1$)(R$^2$)(O)$_p$]$_n$R$^3$ and —[C(R$^1$)(R$^2$)(O)$_p$]$_n$R$^5$, X is hydrogen or 3 to 6 membered heterocyclyl; m, n and o are each independently selected from the group consisting of 1, 2, 3, 4, 5 and 6; p and q are each independently selected from 0.

In an alternative embodiment of the present disclosure, in the compound of formula II, Y is selected from the group consisting of —C(O)O[C(R$^1$)(R$^2$)]$_m$R$^3$, —C(O)NR$^4$[C(R$^1$)(R$^2$)]$_m$R$^3$, —[C(R$^1$)(R$^2$)O]$_m$C(O)[C(R$^1$)(R$^2$)]$_n$R$^3$, —[C(R$^1$)(R$^2$)]$_m$C(O)[OC(R$^1$)(R$^2$)]$_n$R$^3$, —[C(R$^1$)(R$^2$)N]$_m$C(O)[C(R$^1$)(R$^2$)]$_n$R$^3$, —[C(R$^1$)(R$^2$)N]$_m$C(O)[OC(R$^1$)(R$^2$)]$_n$R$^3$, [C(R$^1$)(R$^2$)N]$_m$C(O)[NC(R$^1$)(R$^2$)]$_n$R$^3$, —[C(R$^1$)(R$^2$)(O)$_p$]$_m$C(O)NR$^4$[C(R$^1$)(R$^2$)(O)$_p$]$_n$R$^3$ and —[C(R$^1$)(R$^2$)(O)$_p$]$_n$R$^5$, X is hydrogen or 3 to 6 membered heterocyclyl; m, n and o are each independently selected from the group consisting of 1, 2, 3, 4, 5 and 6; p and q are each independently selected from 1.

In an alternative embodiment of the present disclosure, in the compound of formula II, Y is selected from the group consisting of —C(O)O[C(R$^1$)(R$^2$)]R$^3$, —C(O)NR$^4$[C(R$^1$)(R$^2$)]R$^3$, —[C(R$^1$)(R$^2$)O]C(O)[C(R$^1$)(R$^2$)]R$^3$, —[C(R$^1$)(R$^2$)]C(O)[OC(R$^1$)(R$^2$)]R$^3$, —[C(R$^1$)(R$^2$)N]C(O)[C(R$^1$)(R$^2$)]R$^3$, [C(R$^1$)(R$^2$)N]C(O)[OC(R$^1$)(R$^2$)]R$^3$, [C(R$^1$)(R$^2$)N]C(O)[NC(R$^1$)(R$^2$)]R$^3$, —[C(R$^1$)(R$^2$)(O)$_p$]C(O)NR$^4$[C(R$^1$)(R$^2$)(O)$_p$]R$^3$ and —[C(R$^1$)(R$^2$)(O)$_p$]R$^5$, X is hydrogen or 3 to 6 membered heterocyclyl.

In an alternative embodiment of the present disclosure, in the compound of formula II, Y is selected from the group consisting of —C(O)O[C(R$^1$)(R$^2$)]$_2$R$^3$, —C(O)NR$^4$[C(R$^1$)(R$^2$)]$_2$R$^3$, —[C(R$^1$)(R$^2$)O]$_2$C(O)[C(R$^1$)(R$^2$)]$_2$R$^3$, —[C(R$^1$)(R$^2$)]$_2$C(O)[OC(R$^1$)(R$^2$)]$_2$R$^3$, —[C(R$^1$)(R$^2$)N]$_2$C(O)[C(R$^1$)(R$^2$)]$_2$R$^3$, [C(R$^1$)(R$^2$)N]$_2$C(O)[OC(R$^1$)(R$^2$)]$_2$R$^3$, [C(R$^1$)(R$^2$)N]$_2$C(O)[NC(R$^1$)(R$^2$)]$_2$R$^3$, —[C(R$^1$)(R$^2$)(O)$_p$]$_2$C(O)NR$^4$[C(R$^1$)(R$^2$)(O)$_p$]$_2$R$^3$ and —[C(R$^1$)(R$^2$)(O)$_p$]$_2$R$^5$, X is hydrogen or 3 to 6 membered heterocyclyl.

In an alternative embodiment of the present disclosure, in the compound of formula II, X is selected from the group consisting of —C(O)O[C(R$^1$)(R$^2$)]$_m$R$^3$, —C(O)NR$^4$[C(R$^1$)(R$^2$)]$_m$R$^3$, —[C(R$^1$)(R$^2$)O]$_m$C(O)[C(R$^1$)(R$^2$)]$_n$R$^3$, —[C(R$^1$)(R$^2$)]$_m$C(O)[OC(R$^1$)(R$^2$)]$_n$R$^3$ and —[C(R$^1$)(R$^2$)]$_n$R$^5$, Y is hydrogen.

In an alternative embodiment of the present disclosure, in the compound of formula II, X is selected from the group consisting of —C(O)O[C(R$^1$)(R$^2$)]$_m$R$^3$, —C(O)NR$^4$[C(R$^1$)(R$^2$)]$_m$R$^3$, —[C(R$^1$)(R$^2$)O]$_m$C(O)[C(R$^1$)(R$^2$)]$_n$R$^3$, —[C(R$^1$)(R$^2$)]$_m$C(O)[OC(R$^1$)(R$^2$)]$_n$R$^3$ and —[C(R$^1$)(R$^2$)]$_n$R$^5$; Y is hydrogen; m, n and o are each independently selected from the group consisting of 1, 2, 3, 4, 5 and 6; p and q are each independently selected from 0.

In an alternative embodiment of the present disclosure, in the compound of formula II, X is selected from the group consisting of —[C(R$^1$)(R$^2$)]C(O)[OC(R$^1$)(R$^2$)]R$^3$, —C(O)O[C(R$^1$)(R$^2$)]R$^3$, —C(O)NR$^4$[C(R$^1$)(R$^2$)]R$^3$, —[C(R$^1$)(R$^2$)O]C(O)[C(R$^1$)(R$^2$)]R$^3$, —[C(R$^1$)(R$^2$)]C(O)NR$^4$[C(R$^1$)(R$^2$)]R$^3$ and —[C(R$^1$)(R$^2$)]R$^5$, Y is hydrogen.

Furthermore, in an alternative embodiment of the present disclosure, in the compound of formula II, R$^3$ is selected from the group consisting of hydrogen, poly(oxyethyleneoxy)

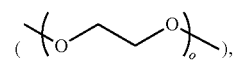

poly(ethyleneoxy)

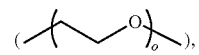

OPO(R$^6$)$_2$, PO(R$^6$)$_2$, OSO$_2$(R$^6$)$_2$, SO$_2$(R$^6$)$_2$, OC(O)R$^6$ and C(O)OR$^6$, R$^6$ is as defined in the compound of formula II.

In an alternative embodiment of the present disclosure, in the compound of formula II, Y is selected from the group consisting of —C(O)O[C(R$^1$)(R$^2$)]$_m$R$^3$, —C(O)NR$^4$[C(R$^1$)(R$^2$)]$_m$R$^3$, —[C(R$^1$)(R$^2$)O]$_m$C(O)[C(R$^1$)(R$^2$)]$_n$R$^3$, —[C(R$^1$)(R$^2$)]$_m$C(O)[OC(R$^1$)(R$^2$)]$_n$R$^3$, —[C(R$^1$)(R$^2$)N]$_m$C(O)[C(R$^1$)(R$^2$)]$_n$R$^3$, [C(R$^1$)(R$^2$)N]$_m$C(O)[OC(R$^1$)(R$^2$)]$_n$R$^3$, [C(R$^1$)(R$^2$)N]$_m$C(O)[NC(R$^1$)(R$^2$)]$_n$R$^3$, —[C(R$^1$)(R$^2$)(O)$_p$]$_m$C(O)NR$^4$[C(R$^1$)(R$^2$)(O)$_p$]$_n$R$^3$ and —[C(R$^1$)(R$^2$)(O)$_p$]$_n$R$^5$, X is hydrogen or 3 to 6 membered heterocyclyl; R$^3$ is selected from hydrogen, poly(oxyethyleneoxy)

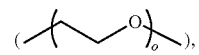

poly(ethyleneoxy)

OPO(R$^6$)$_2$, PO(R$^6$)$_2$, OSO$_2$(R$^6$)$_2$, SO$_2$(R$^6$)$_2$, OC(O)R$^6$ and C(O)OR$^6$, R$^6$ is as defined in the compound of formula II.

In an alternative embodiment of the present disclosure, in the compound of formula II, Y is selected from [C(R$^1$)(R$^2$)(O)$_p$]$_n$R$^5$, R$^5$ is selected from the group consisting of C$_{6-10}$ heterocyclyl, OPO(R$^6$)$_2$, OSO$_2$R$^6$, SR', SO$_2$R',

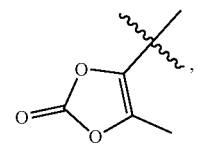 [SMILES: *c1oc(=O)oc1C]

OC(O)R$^7$ and NR'(R").

In an alternative embodiment of the present disclosure, in the compound of formula II, Y is selected from [C(R$^1$)(R$^2$)O]$_n$R$^5$, R$^5$ is selected from the group consisting of C$_{6-10}$ heterocyclyl, OPO(R$^6$)$_2$, OSO$_2$R$^6$, SR', SO$_2$R',

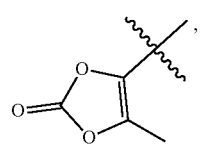 [SMILES: *c1oc(=O)oc1C]

OC(O)R$^7$ and NR'(R").

In an alternative embodiment of the present disclosure, in the compound of formula II, Y is selected from [C(R$^1$)(R$^2$)O]$_n$R$^5$, R$^5$ is selected from the group consisting of C$_{6-10}$ heterocyclyl, OPO(R$^6$)$_2$, OSO$_2$R$^6$, SR', SO$_2$R',

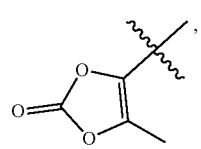 [SMILES: *c1oc(=O)oc1C]

OC(O)R$^7$ and NR'(R").

In an alternative embodiment of the present disclosure, in the compound of formula II, $R^5$ is selected from the group consisting of $C_{6-10}$ heterocyclyl, $OPO(R^6)_2$, $OSO_2R^6$, $SR'$, $SO_2R'$,

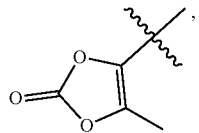

$OC(O)R^7$ and $NR'(R'')$.

Furthermore, in the compound of formula II, said $R^6$ is selected from the group consisting of hydrogen, $C_{1-6}$ alkyl, $C_{3-6}$ cycloalkyl, 3 to 6 membered heterocyclyl (such as piperidine), $OR'$ and $NR'(R'')$, $R'$ and $R''$ are as defined in the compound of formula II.

In an alternative embodiment of the present disclosure, in the compound of formula II, $R'$ and $R''$ are selected from the group consisting of hydrogen and alkyl, said alkyl is preferably selected from $C_{1-10}$ alkyl, more preferably selected from $C_{1-6}$ alkyl, such as methyl, ethyl, propyl and isopropyl.

In an alternative embodiment of the present disclosure, in the compound of formula II, wherein m=1, 2, 3 or 4, n=1, 2, 3 or 4, and o=1~8.

In some embodiments, in the compound of formula II, $R^6$ and $R^7$ are each independently selected from the group consisting of:

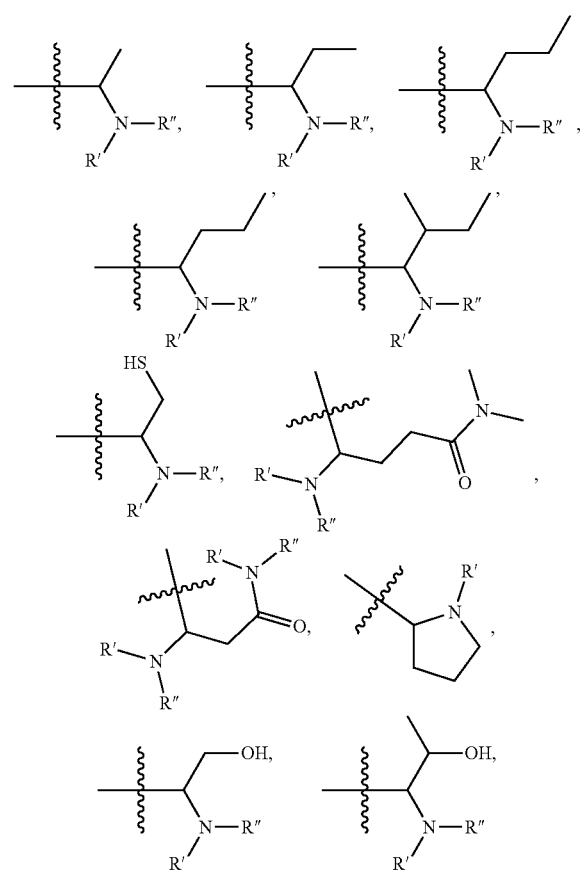

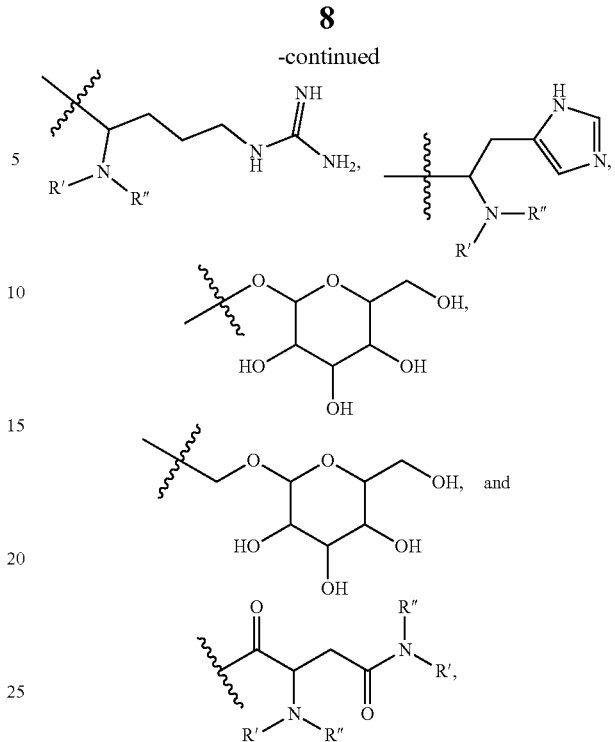

wherein $R'$ and $R''$ are selected from the group consisting of hydrogen and alkyl, said alkyl is preferably selected from $C_{1-10}$ alkyl, more preferably selected from $C_{1-6}$ alkyl, such as methyl, ethyl, propyl and isopropyl.

In some embodiments, provided is the compound of II, $R^3$ is selected from $OPO(R^6)_2$, $R^6$ is selected from the group consisting of hydroxyl, $C_{1-6}$ alkyl, $C_{3-7}$ cycloalkyl, $C_{1-6}$ alkoxyl and 3 to 7 membered heterocyclyl.

In some other embodiments, provided is the compound of II, wherein m=1, 2, 3 or 4.

In some other embodiments, provided is the compound of II, wherein $R^1$ and $R^2$ are each independently selected from the group consisting of hydrogen, $C_{1-6}$ alkyl and $C_{3-7}$ cycloalkyl.

In some other embodiments, the compound of formula II is

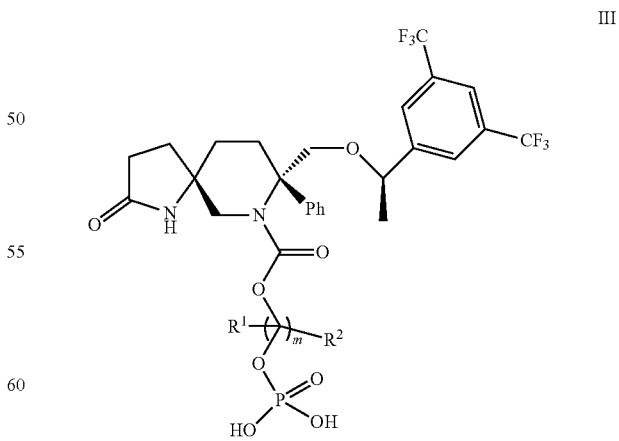

or a pharmaceutically acceptable salt thereof, or a stereoisomer, rotamer or tautomer thereof, or a deuteride thereof, wherein, $R^1$ and $R^2$ are each independently selected from the group consisting of hydrogen, alkyl, cycloalkyl, heterocyclyl, aryl and heteroaryl, said alkyl, cycloalkyl, heterocyclyl, aryl or heteroaryl is optionally substituted with one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R"), COOR' and CONR'(R");

R' and R" are each independently selected from the group consisting of hydrogen, hydroxyl, alkyl, alkoxyl, alkenyl and acyl;

m=1, 2, 3 or 4.

In some embodiments, in the compound of formula II, $R^6$ is selected from the group consisting of:

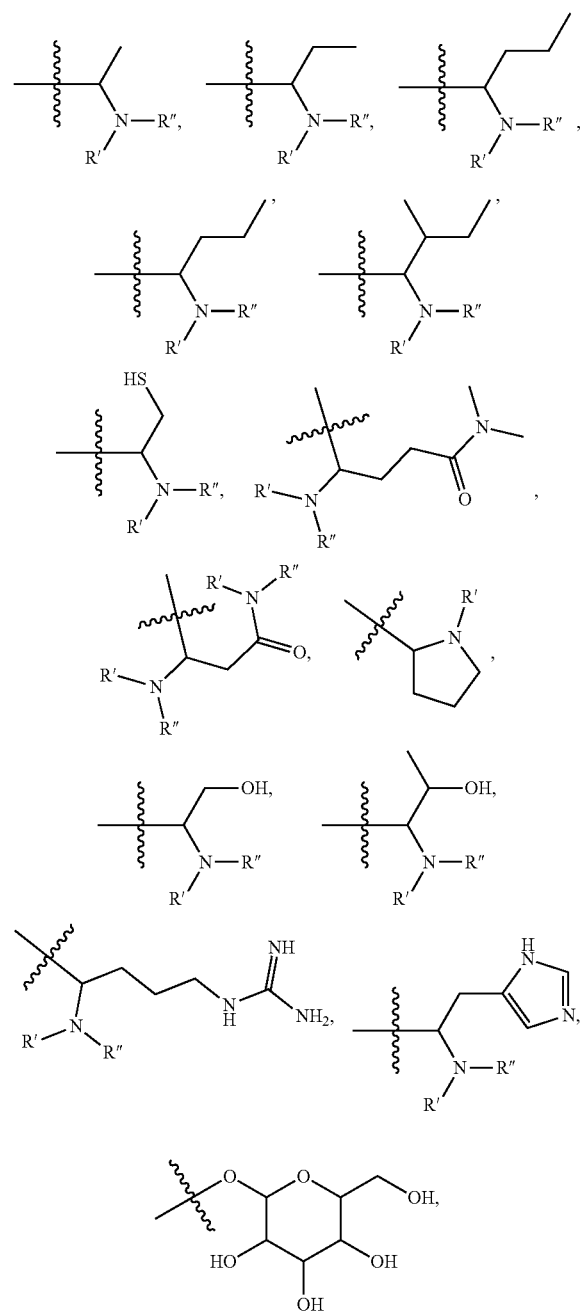

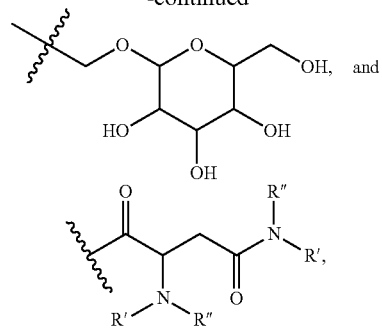

wherein R' and R" are selected from the group consisting of hydrogen and alkyl, said alkyl is preferably selected from $C_{1-10}$ alkyl, more preferably selected from $C_{1-6}$ alkyl, such as methyl, ethyl, propyl and isopropyl.

In some other embodiments, the compound of formula III is

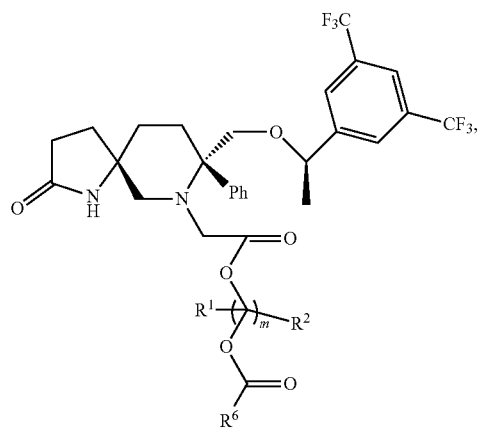

IV or a pharmaceutically acceptable salt thereof, or a stereoisomer, rotamer or tautomer thereof, or a deuteride thereof, wherein, $R^1$ and $R^2$ are each independently selected from the group consisting of hydrogen, alkyl, cycloalkyl, heterocyclyl, aryl and heteroaryl, said alkyl, cycloalkyl, heterocyclyl, aryl or heteroaryl is optionally substituted with one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R"), COOR' and CONR'(R");

each of $R^6$ is independently selected from the group consisting of hydrogen, hydroxyl, alkyl, cycloalkyl, heterocyclyl, aryl, heteroaryl, alkoxyl, hydroxyalkyl and NR'(R"), said alkyl, hydroxyalkyl, cycloalkyl, heterocyclyl, aryl or heteroaryl is optionally substituted with one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R"), COOR' and CONR'(R");

R' and R" are each independently selected from the group consisting of hydrogen, hydroxyl, alkyl, alkoxyl, alkenyl and acyl.

Furthermore, in an alternative embodiment, in the compound of formula IV, $R^6$ is selected from the group consisting of $C_{1-12}$ alkyl (including but not limited to methyl, ethyl, propyl or isopropyl), $C_{3-12}$ cycloalkyl (including but not limited to cyclopropyl, cyclopentyl, cyclohexyl), 3 to 12 membered heterocyclyl (including but not limited to pyrrolyl), $C_{6-12}$ aryl (including but not limited to phenyl, naphthyl), 3 to 12 membered heteroaryl (including but not limited to pyridine, piperidine), $C_{1-12}$ alkoxyl (including but not limited to methoxyl, ethoxyl, propoxyl or isopropoxyl), $C_{1-12}$ hydroxyalkyl and NR'(R"), said alkyl, hydroxyalkyl, cycloalkyl, heterocyclyl, aryl or heteroaryl is optionally substituted with one or more groups selected from the group consisting of $C_{1-6}$ alkyl, $C_{3-6}$ cycloalkyl, 3 to 12 membered heterocyclyl, $C_{1-12}$ alkoxyl, $C_{1-6}$ hydroxyalkyl, $C_{2-4}$ alkenyl, $C_{2-4}$ alkynyl, $C_{6-10}$ aryl, 3 to 10 membered heteroaryl, nitro, cyano, hydroxyl, halogen, SR', NR'(R"), COOR' and CONR'(R"); R' and R" are each independently selected from the group consisting of hydrogen, $C_{1-6}$ alkyl, $C_{1-6}$ alkoxyl, $C_{2-4}$ alkenyl, $C_{1-6}$ alkanoyl (such as acetyl, formyl), benzoyl and p-toluoyl.

In a preferred embodiment of the present disclosure, in the compound of formula II, said $R^6$ is selected from the group consisting of hydrogen, $C_{1-6}$ alkyl, $C_{3-6}$ cycloalkyl, 3 to 6 membered heterocyclyl (such as piperidine), OR' and NR'(R").

In an alternative embodiment of the present disclosure, in the compound of formula IV, R' and R" are selected from the group consisting of hydrogen and alkyl, said alkyl is preferably selected from $C_{1-10}$ alkyl, more preferably selected from $C_{1-6}$ alkyl, such as methyl, ethyl, propyl and isopropyl.

In some embodiments, in the compound of formula IV, $R^6$ is selected from the group consisting of:

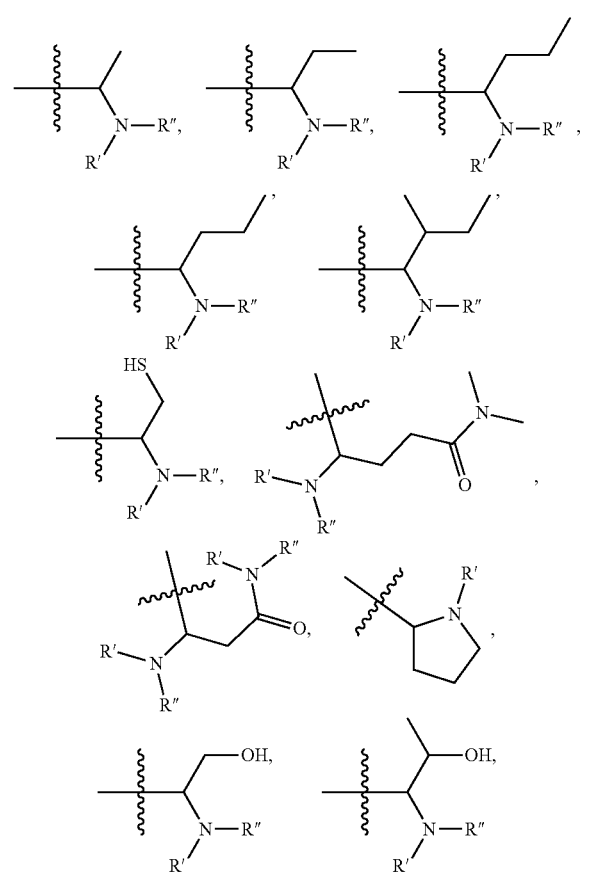

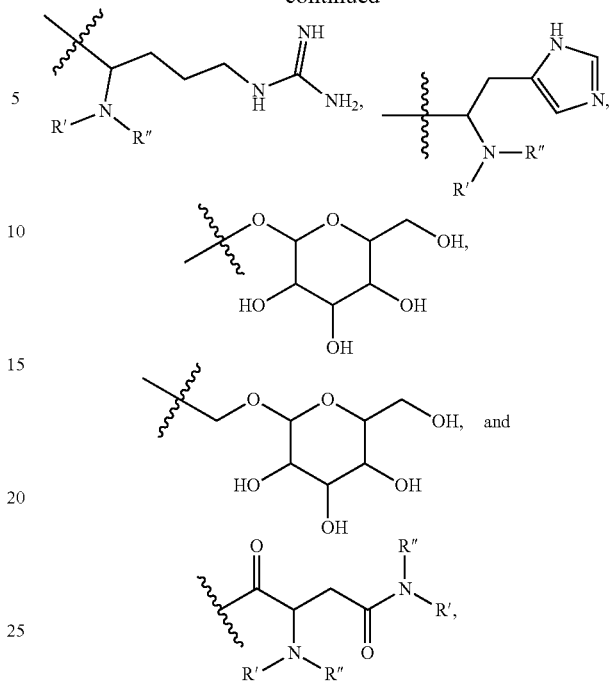

wherein R' and R" are selected from the group consisting of hydrogen and alkyl, said alkyl is preferably selected from $C_{1-10}$ alkyl, more preferably selected from $C_{1-6}$ alkyl, such as methyl, ethyl, propyl and isopropyl.

In a preferred embodiment of the present disclosure, in the compound of formula II, said $R^6$ is selected from the group consisting of hydrogen, $C_{1-6}$ alkyl, $C_{3-6}$ cycloalkyl, 3 to 6 membered heterocyclyl (such as piperidine), OR' and NR'(R").

In an alternative embodiment of the present disclosure, in the compound of formula IV, wherein R' and R" are selected from the group consisting of hydrogen and alkyl, said alkyl is preferably selected from $C_{1-10}$ alkyl, more preferably selected from $C_{1-6}$ alkyl, such as methyl, ethyl, propyl and isopropyl.

In some other embodiments, in the compound of formula IV, $R^6$ is selected from the group consisting of:

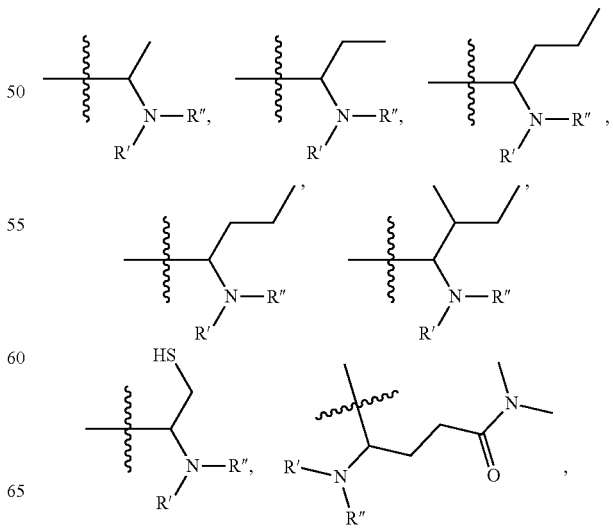

-continued
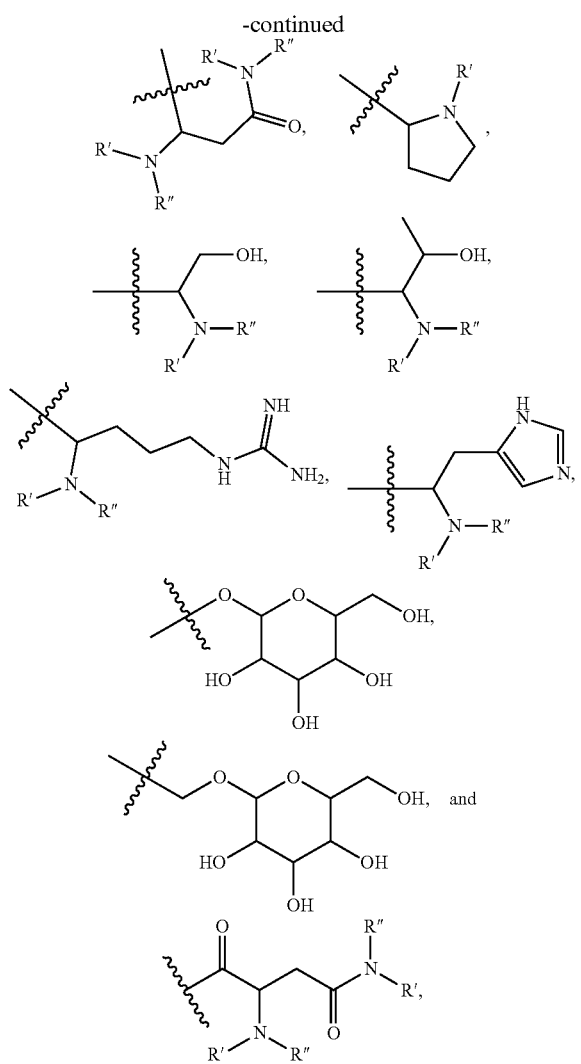
wherein R' and R" are selected from the group consisting of hydrogen and alkyl, said alkyl is preferably selected from $C_{1-10}$ alkyl, more preferably selected from $C_{1-6}$ alkyl, such as methyl, ethyl, propyl and isopropyl.
Typical compounds of formula II include, but are not limited to:
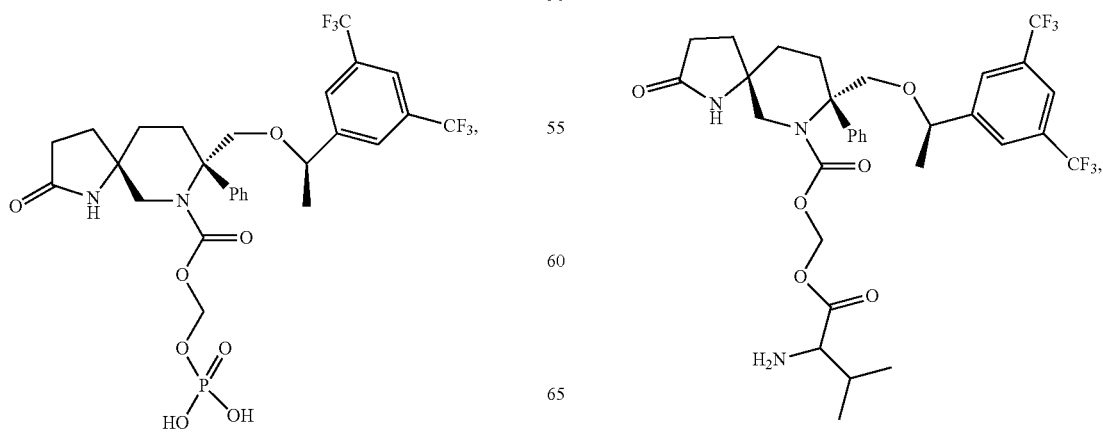
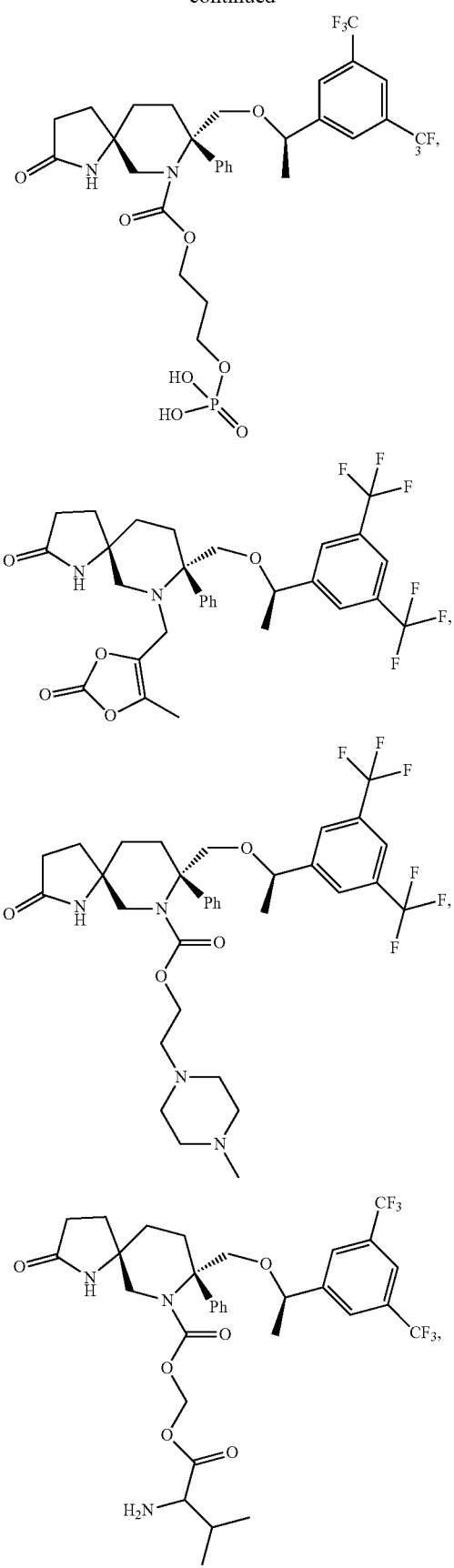

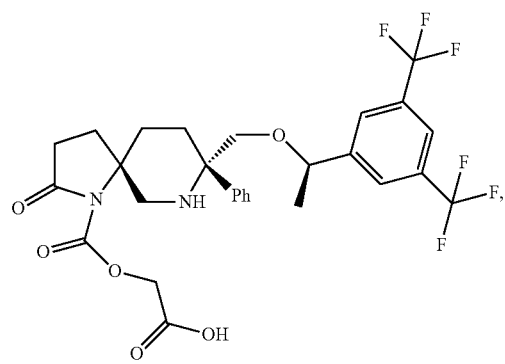
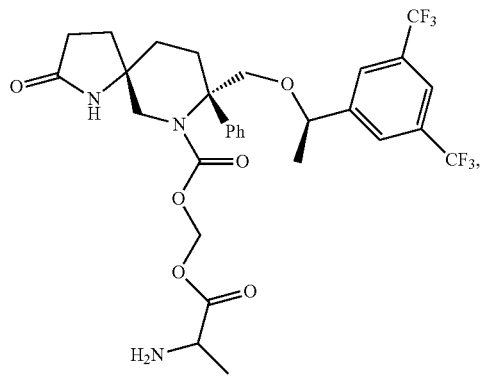
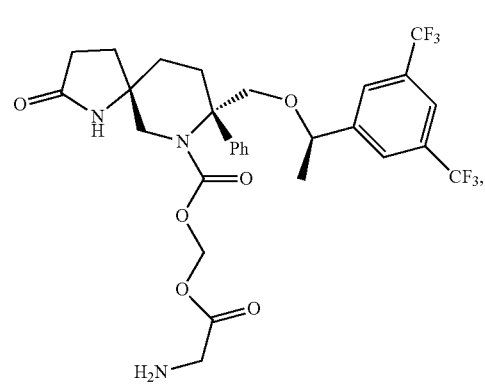
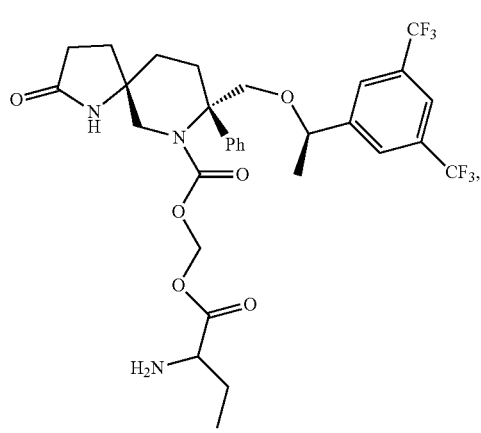
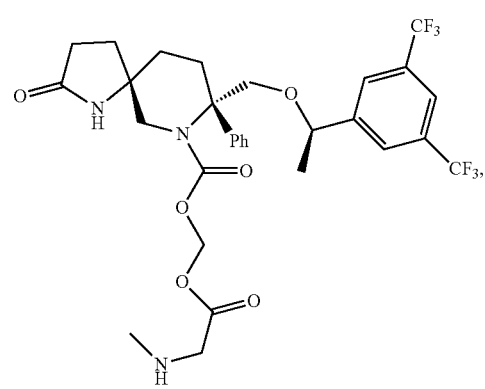
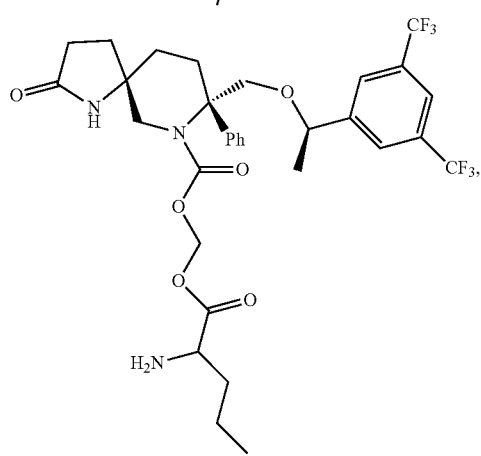
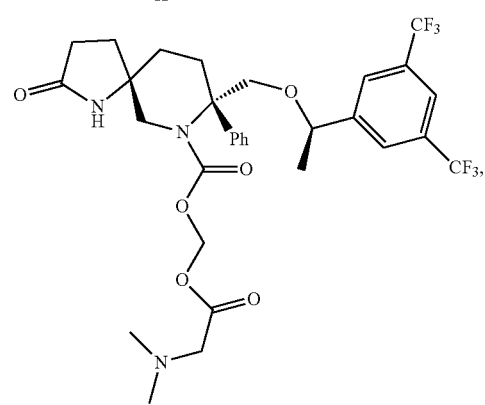
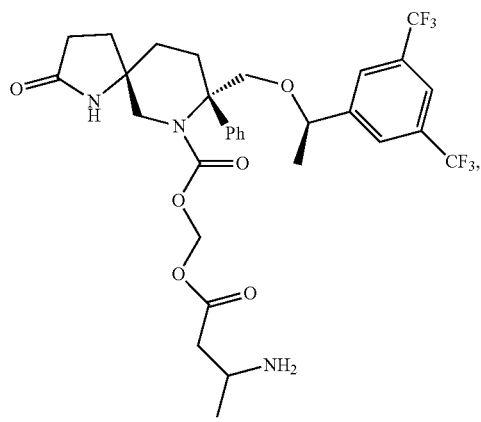

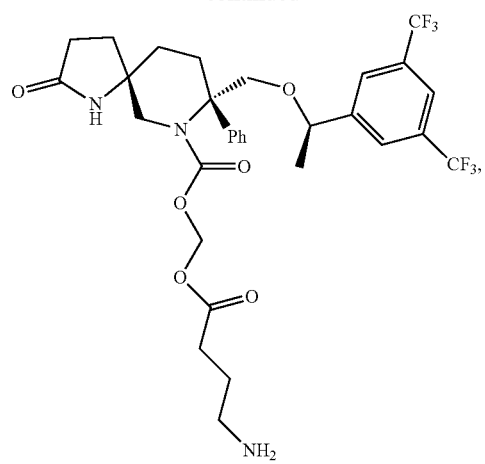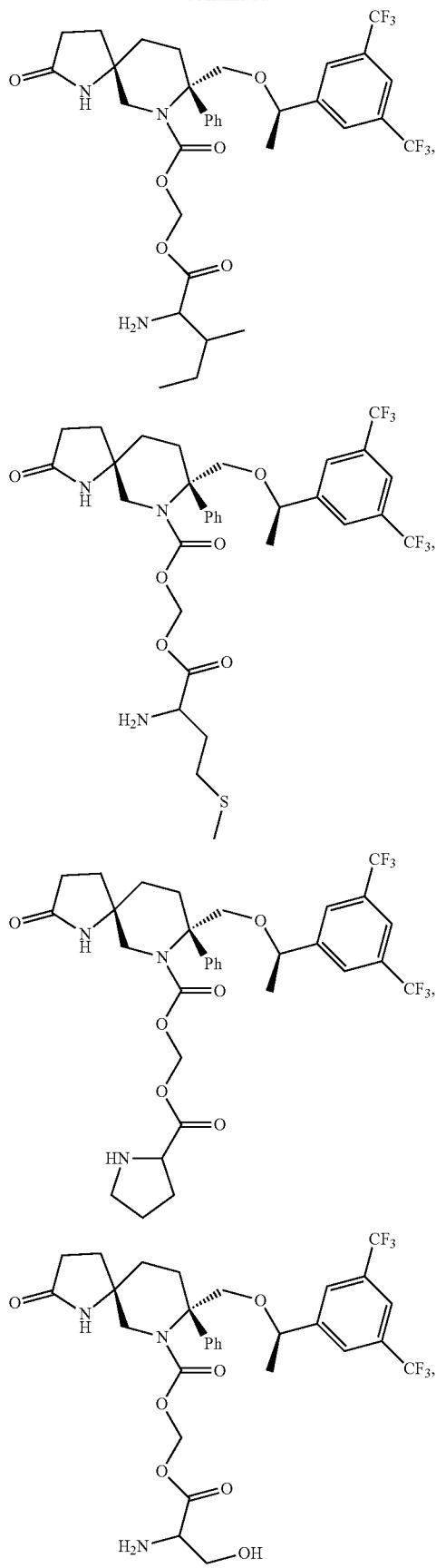

-continued
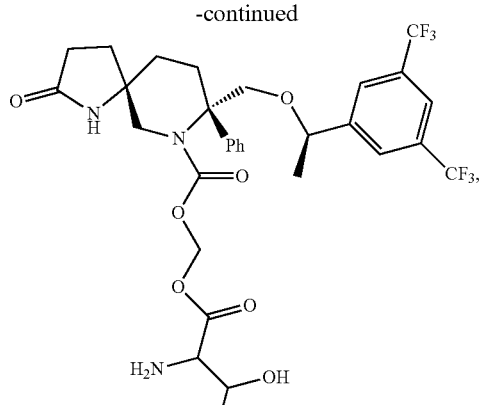
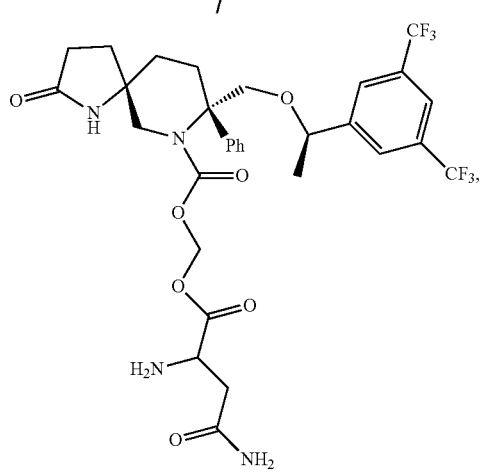
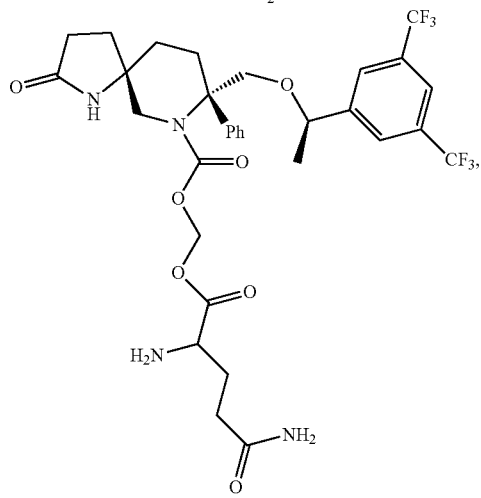
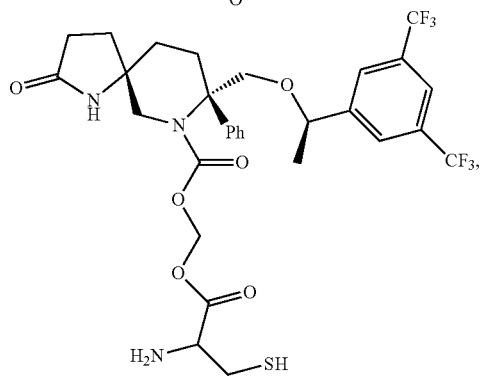
-continued
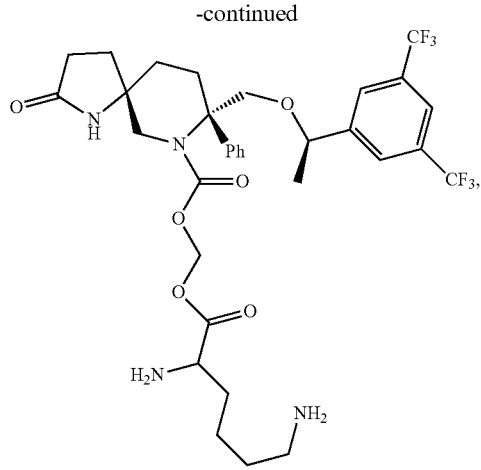
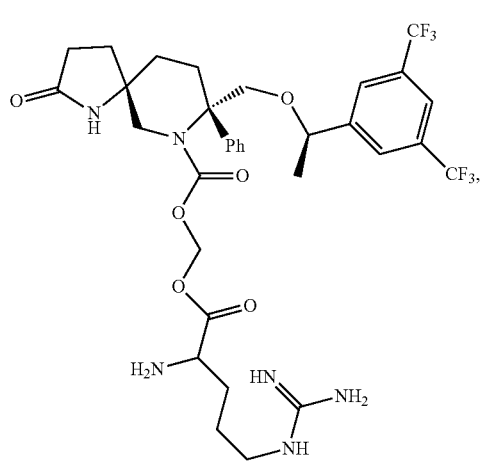
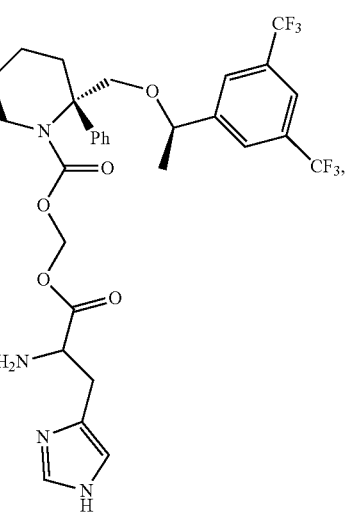

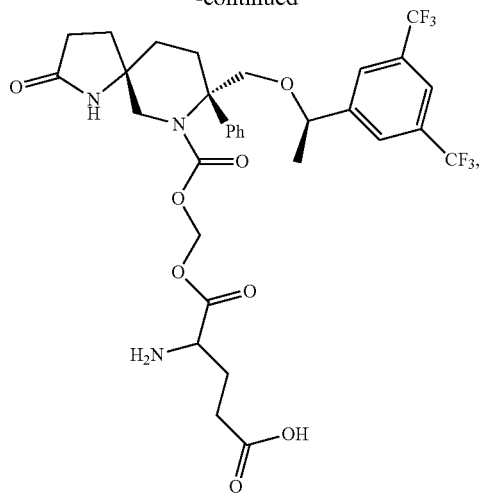
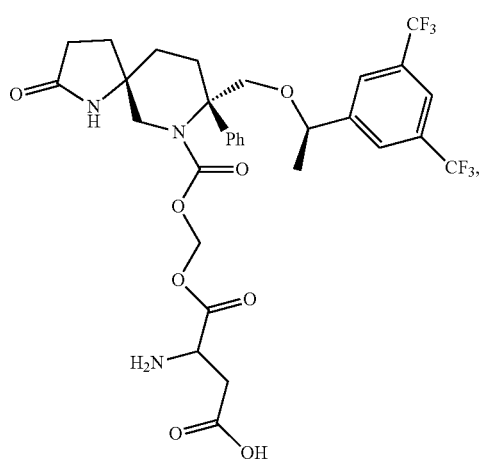
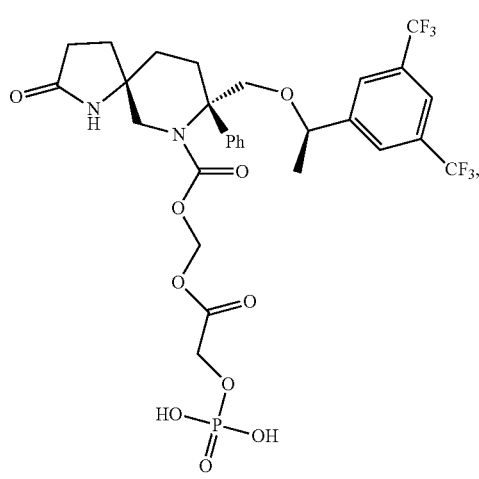
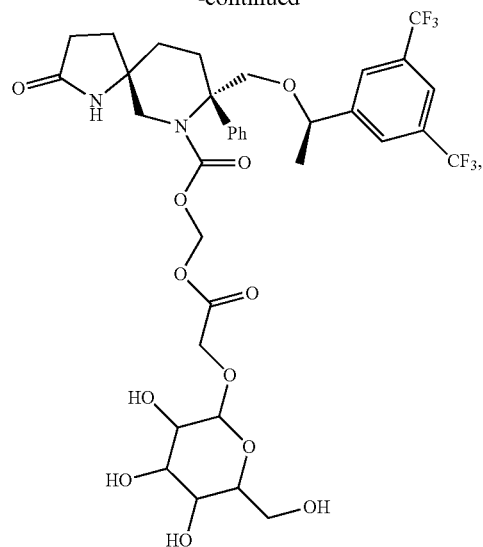
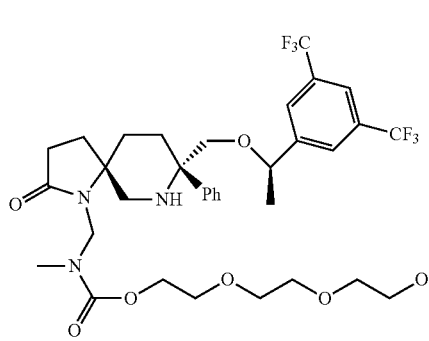
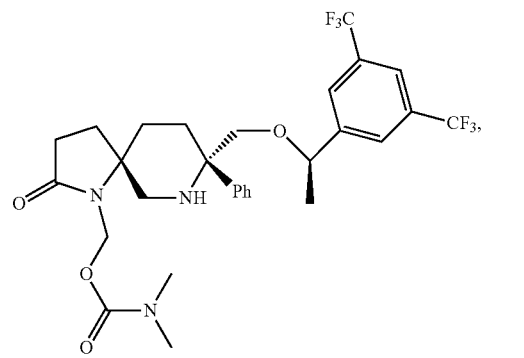
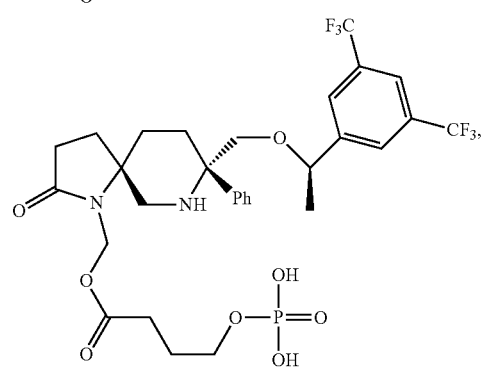

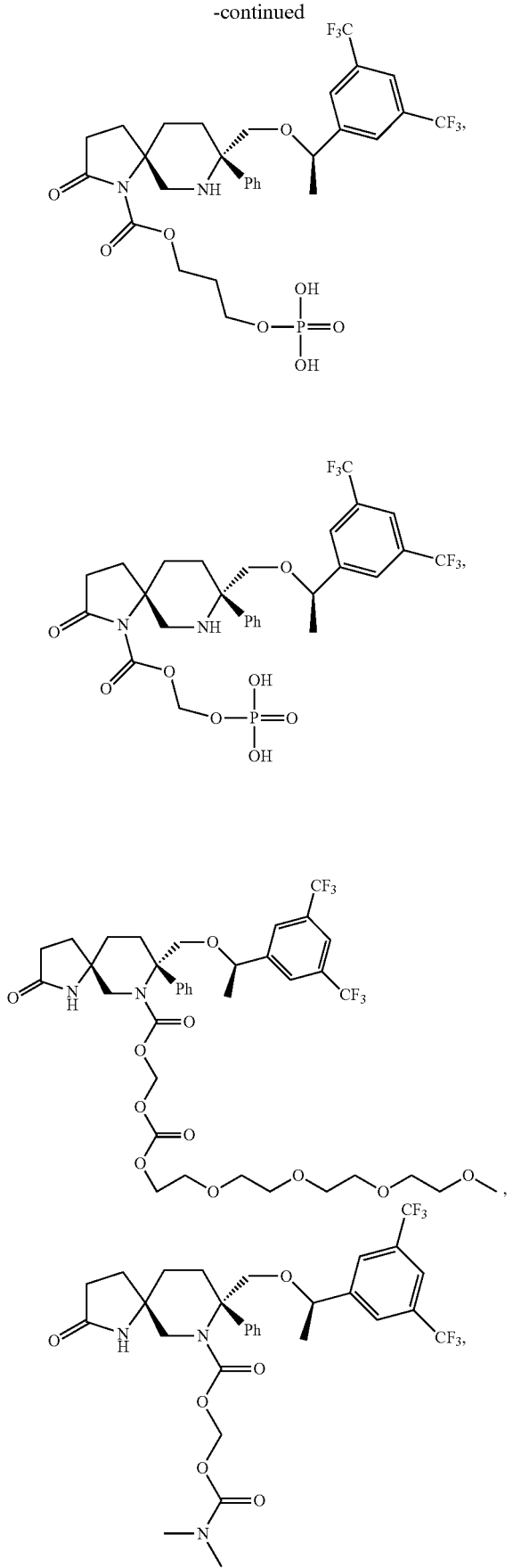
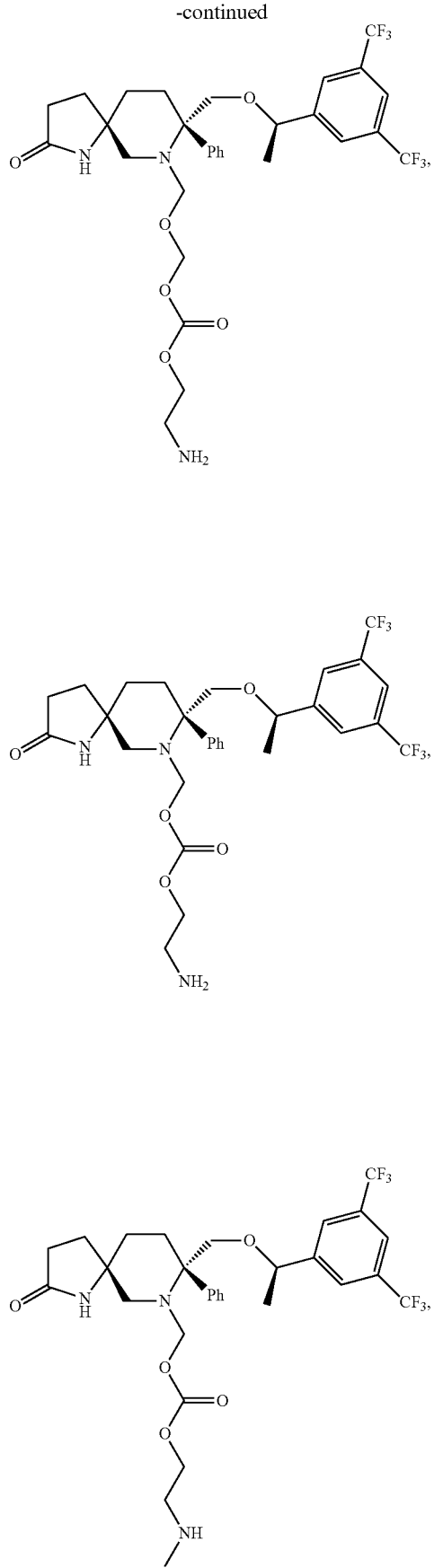

-continued
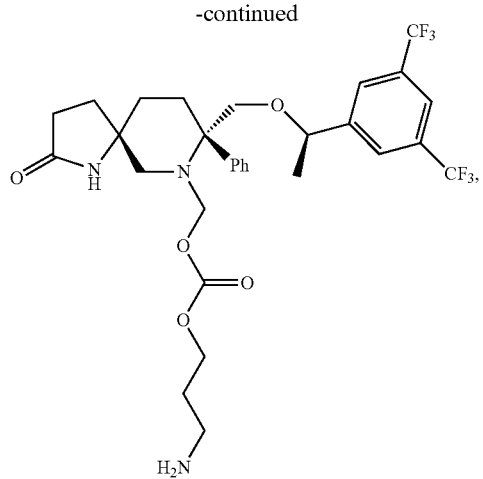
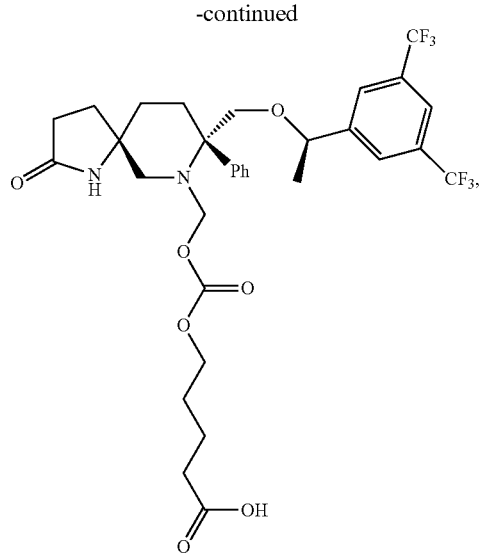
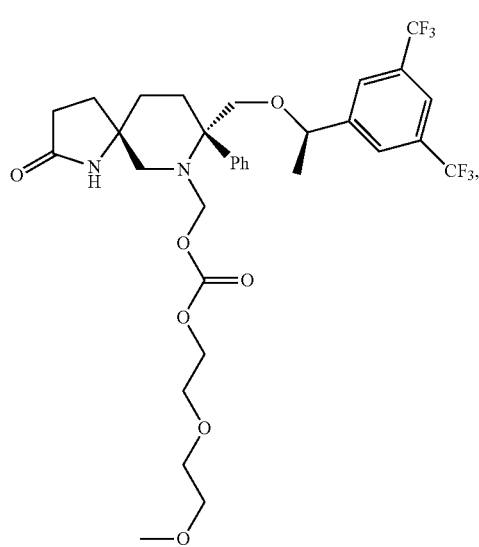
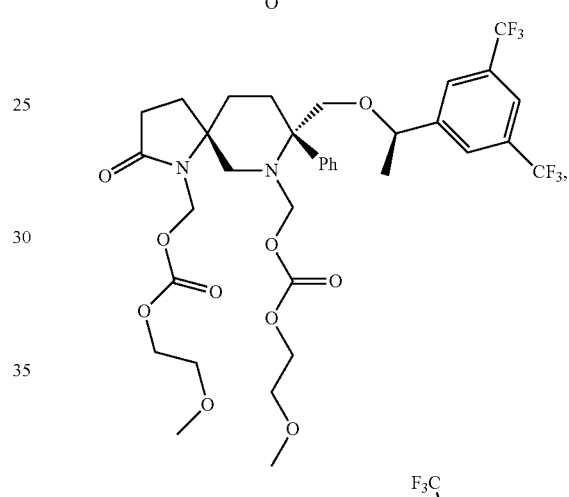
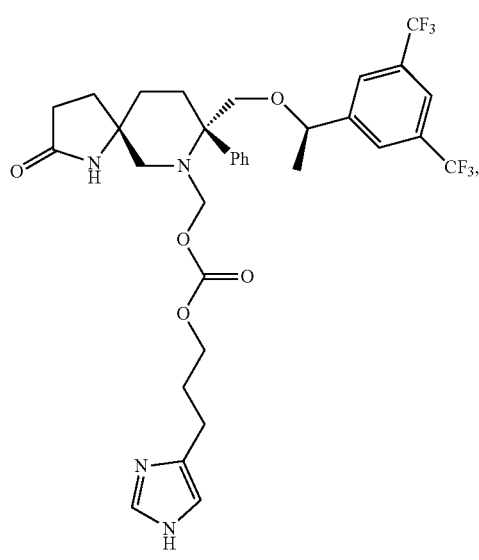
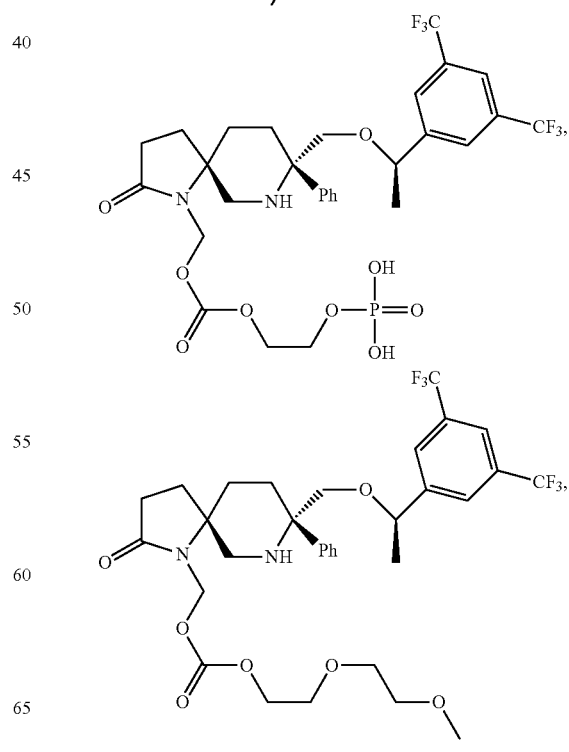

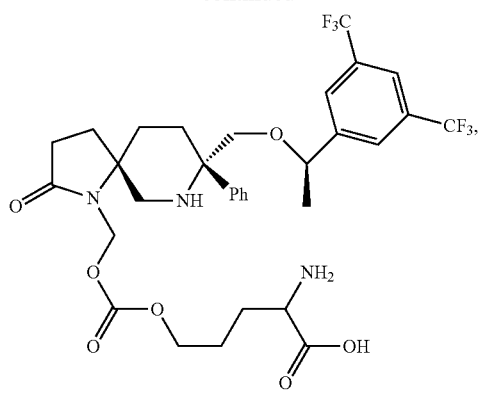

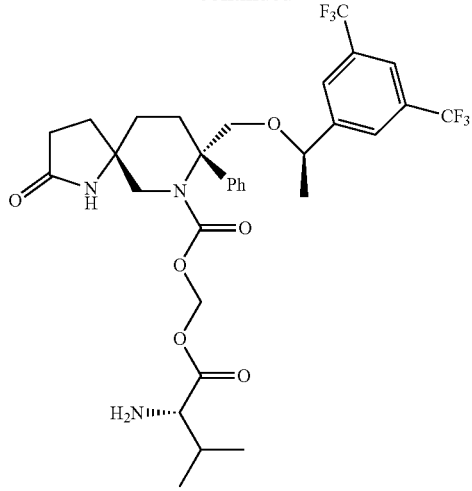

or a pharmaceutically acceptable salt thereof.

In another aspect, the compound of the present disclosure has higher solubility and better in vivo conversion compared with known compounds. In some embodiments, the compound of the present disclosure has low hemolytic effect and reduced side effects after drug administration, and is beneficial to improve patient compliance with the drug administration.

The present disclosure also provides a pharmaceutical composition comprising a therapeutically effective amount of at least one of the aforementioned compounds or a pharmaceutically acceptable salt thereof, as well as a pharmaceutically acceptable carrier, diluent or excipient.

In another aspect, the hydrogen in the functional group of the compound according to the present disclosure can be deuterated to obtain the corresponding deuterated compound, which retains the selectivity and potential comparable to the hydrogen analog. The deuterium bond is more stable, leading to different "ADME", i.e. "toxic pharmacokinetics", thereby providing clinically beneficial effects.

Toxic pharmacokinetics refers to the processes of absorption, distribution, metabolism and excretion of exogenous chemicals by the body.

The present disclosure also relates to a use of the compound, or a pharmaceutically acceptable salt thereof, or the pharmaceutical composition according to the above embodiments in the preparation of medicaments for the treatment of physiological disorders, conditions or diseases in a patient, wherein the physiological disorder, condition or disease is respiratory disease, cough, inflammatory disease, skin disorder, ophthalmological disorder, depression, anxiety, phobias, bipolar disorder, alcohol dependence, substance abuse with significant effect on nerves, epilepsy, nociception, psychosis, schizophrenia, Alzheimer's disease, AIDS-related dementia, Towne's disease, stress-related disorder, obsessive/compulsive disorder, bulimia, anorexia nervosa, binge eating, mania, premenstrual syndrome, gastrointestinal dysfunction, atherosclerosis, fibrotic disorder, obesity, type II diabetes, headache, neuropathic pain, post-action pain, chronic pain syndrome, bladder disorder, genitourinary disorder or vomiting or nausea, further relates to the use for the preparation of medicaments for the treatment of asthma, vomiting, nausea, depression, anxiety, cough or migraine.

In another aspect, the pharmaceutically acceptable salt of the compound is selected from the group consisting of inorganic salt and organic salt. The compound according to

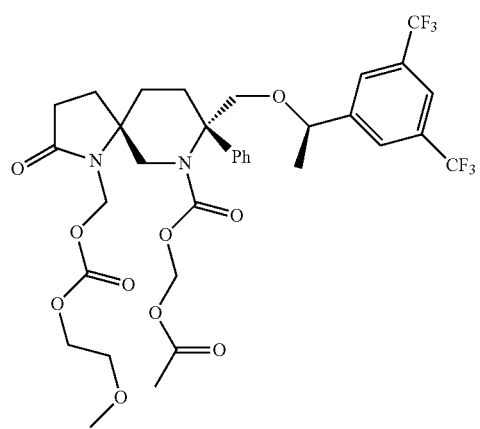 [SMILES: COCCOC(=O)OCN1C(=O)CC[C@]12CC[C@@](CO[C@H](C)c1cc(C(F)(F)F)cc(C(F)(F)F)c1)(c1ccccc1)N(C(=O)OCOC(C)=O)C2]

or a pharmaceutically acceptable salt thereof, a stereoisomer, rotamer or tautomer thereof.

Furthermore, the compound of formula IA is:

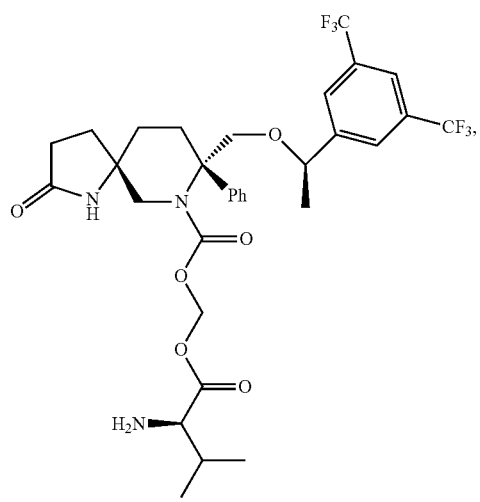

the present disclosure is reacted with an acid such as trifluoroacetic acid to form the corresponding salt. Said acid is selected from the group consisting of, but not limited to, acetic acid, hydrochloric acid, salicylic acid, malic acid, ascorbic acid, phosphoric acid, citric acid, benzoic acid and fumaric acid. The compound according to the present disclosure is reacted with a base such as N-methyl-D meglumine or dicyclohexylamine to form the corresponding salt. Said base is selected from the group consisting of, but not limited to, sodium, alkaline earth metal and amino acid (such as arginine, lysine).

In another aspect, the present disclosure also includes isotope-labeled compounds of the present application, which are the same as those described in the present disclosure, but with one or more atoms being replaced by atoms having atomic weight or mass number different from that commonly found in nature. Examples of isotopes that can be incorporated into the compounds of the present application include isotopes of hydrogen, carbon, nitrogen, oxygen, phosphorus, sulfur, fluorine, iodine and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^5$S, $^{18}$F, $^{123}$I, $^{125}$I and $^{36}$Cl, and the like.

The compounds of the present disclosure can comprise an unnatural proportion of atomic isotopes in one or more of the atoms constituting the compound. For example, the compounds can be labeled with radioisotopes, such as tritium ($^3$H), iodine-125 ($^{125}$I) or C-14 ($^{14}$C). For another example, a hydrogen can be replaced by a deuterium to form deuteride. The bond between deuterium and carbon is stronger than the bond between normal hydrogen and carbon. Compared with undeuterated compounds, deuterated compounds have the advantages of reduced toxic and side effects, increased drug stability, enhanced efficacy, prolonged biological half-life, and the like. All changes in the isotopic composition of the compounds of the present application, whether radioactive or not, are included in the scope of the present application.

In addition, substitution with heavier isotopes (such as deuterium (i.e. $^2$H)) can provide certain therapeutic advantages resulting from higher metabolic stability (for example, increased in vivo half-life or reduced dosage requirements), and therefore can be preferred under certain circumstances, wherein the deuterium substitution can be partial or complete, and partial deuterium substitution refers to replacing at least one hydrogen by at least one deuterium.

Explanation of Terms

"Alkyl" refers to a saturated aliphatic hydrocarbon group, including a straight or branched group with 1 to 20 carbon atoms, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, and various branched isomers thereof. The alkyl can be substituted or unsubstituted. When substituted, the substituent group(s) can be substituted at any available connection point. The substituent group(s) is preferably one or more groups independently selected from the group consisting of aryl, heteroaryl and halogen.

"Alkenyl" refers to a branched or straight olefin with 2 to 12 carbon atoms or an olefin containing aliphatic hydrocarbon groups. For example, "$C_{2-6}$ alkenyl" means an alkenyl with 2, 3, 4, 5 or 6 carbon atoms. Examples of alkenyl groups include, but are not limited to vinyl, allyl, 1-propenyl, 1-butenyl, 2-butenyl, 3-butenyl, 2-methylbut-2-enyl, 3-methylbut-1-enyl, 1-pentenyl, 3-pentenyl and 4-hexenyl.

The term "cycloalkyl" refers to a saturated or partially unsaturated monocyclic or polycyclic hydrocarbon substituent. The cycloalkyl ring comprises 3 to 20 carbon atoms, preferably 3 to 12 carbon atoms, more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptantrienyl, cyclooctyl, and the like. Polycyclic cycloalkyl includes a cycloalkyl having a spiro ring, fused ring or bridged ring.

Said cycloalkyl ring can be fused to an aryl, heteroaryl or heterocyclyl ring, wherein the ring attached to the parent structure is the cycloalkyl. Non-limiting examples include indanyl, tetrahydronaphthyl, benzocycloheptyl and the like. The cycloalkyl can be optionally substituted or unsubstituted. When substituted, the substituent is preferably one or more groups independently selected from the group consisting of alkyl, alkenyl, alkynyl, alkoxyl, alkanethio, alkylamino, halogen, thiol, hydroxyl, nitro, cyano, cycloalkyl, heterocyclyl, aryl, heteroaryl, cycloalkoxyl, heterocycloalkoxyl, cycloalkylthio, heterocyclylthio, oxo, carboxyl or carboxylate.

The term "heterocyclyl" refers to a saturated or partially unsaturated monocyclic or polycyclic hydrocarbon substituent, which comprises 3 to 20 ring atoms, wherein one or more ring atoms are heteroatoms selected from the group consisting of nitrogen, oxygen and $S(O)_m$ (wherein m is an integer from 0 to 2), but excluding the ring moiety of —O—O—, —O—S— or —S—S—, with the remaining ring atoms being carbon atoms. Preferably, the heterocyclyl comprises 3 to 12 ring atoms wherein 1 to 4 atoms are heteroatoms; more preferably comprising 3 to 6 ring atoms. Non-limiting examples of monocyclic heterocyclyl include pyrrolidinyl, imidazolidinyl, tetrahydrofuranyl, tetrahydrothiophenyl, dihydroimidazolyl, dihydrofuranyl, dihydropyrazolyl, dihydropyrrolyl, piperidinyl, piperazinyl, morpholinyl, thiomorpholinyl, homopiperazinyl and the like, preferably piperidinyl and pyrrolidinyl. Polycyclic heterocyclyl includes a heterocyclyl having a spiro ring, fused ring or bridged ring.

Said heterocyclic ring can be fused to an aryl, heteroaryl or cycloalkyl ring, wherein the ring attached to the parent structure is the heterocyclyl. Non-limiting examples include:

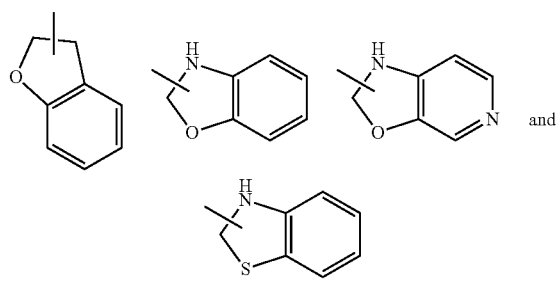

and the like.

The heterocyclyl can be optionally substituted or unsubstituted. When substituted, the substituent group(s) is preferably one or more groups independently selected from the group consisting of alkyl, alkenyl, alkynyl, alkoxyl, alkylthiol, alkylamino, halogen, thiol, hydroxyl, nitro, cyano, cycloalkyl, heterocyclyl, aryl, heteroaryl, cycloalkoxyl, heterocycloalkoxyl, cycloalkylthio, heterocyclylthio, oxo, carboxyl or carboxylate.

"Alkynyl" includes a branched or straight alkynyl with 2 to 12 carbon atoms or an olefin containing aliphatic hydrocarbon groups, or if the number of carbon atoms is specified, it means that specific number, for example, ethynyl, propynyl (for example, 1-propynyl, 2-propynyl), 3-butynyl, pentynyl, hexynyl and 1-methylpent-2-ynyl.

The term "aryl" refers to a 6 to 14 membered all-carbon monocyclic ring or polycyclic fused ring (i.e. each ring shares an adjacent pair of carbon) having a conjugated π-electron system, preferably 6 to 12 membered, for example phenyl or naphthyl. Said aryl ring can be fused to the ring of heteroaryl, heterocyclyl or cycloalkyl, wherein the ring attached to the parent structure is the aryl ring. Non-limiting examples include:

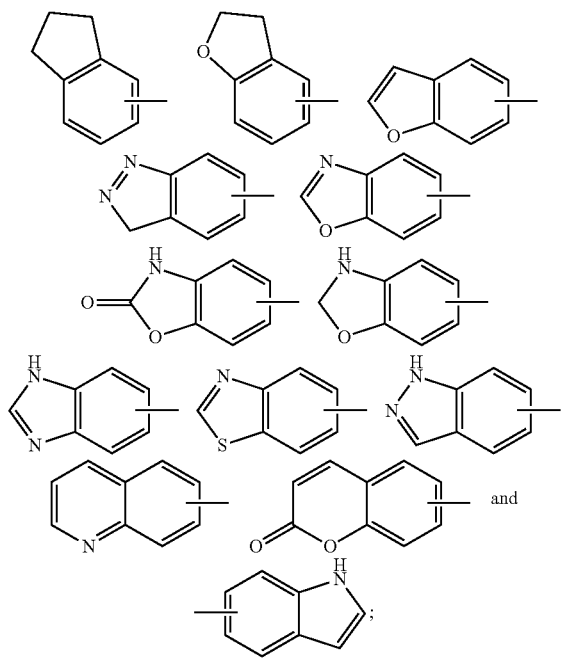

The aryl can be substituted or unsubstituted. When substituted, the substituent group(s) is preferably one or more groups independently selected from the group consisting of alkyl, alkenyl, alkynyl, alkoxyl, alkylthio, alkylamino, halogen, thiol, hydroxyl, nitro, cyano, cycloalkyl, heterocyclyl, aryl, heteroaryl, cycloalkoxyl, heterocycloalkoxyl, cycloalkylthio, heterocyclylthio, carboxyl and carboxylate, preferably phenyl.

The term "heteroaryl" refers to a heteroaromatic system comprising 1 to 4 heteroatoms and 5 to 14 ring atoms, wherein the heteroatom is selected from the group consisting of oxygen, sulfur and nitrogen. The heteroaryl is preferably a 6 to 12 membered heteroaryl, more preferably a 5 or 6 membered heteroaryl, for example imidazolyl, furyl, thienyl, thiazolyl, pyrazolyl, oxazolyl, pyrrolyl, tetrazolyl, pyridyl, pyrimidinyl, thiadiazole, pyrazinyl and the like; preferably imidazolyl, pyrazolyl, pyrimidinyl or thiazolyl; more preferably pyrazolyl or thiazolyl. Said heteroaryl ring can be fused to the ring of aryl, heterocyclyl or cycloalkyl, wherein the ring attached to the parent structure is the heteroaryl ring. Non-limiting examples include:

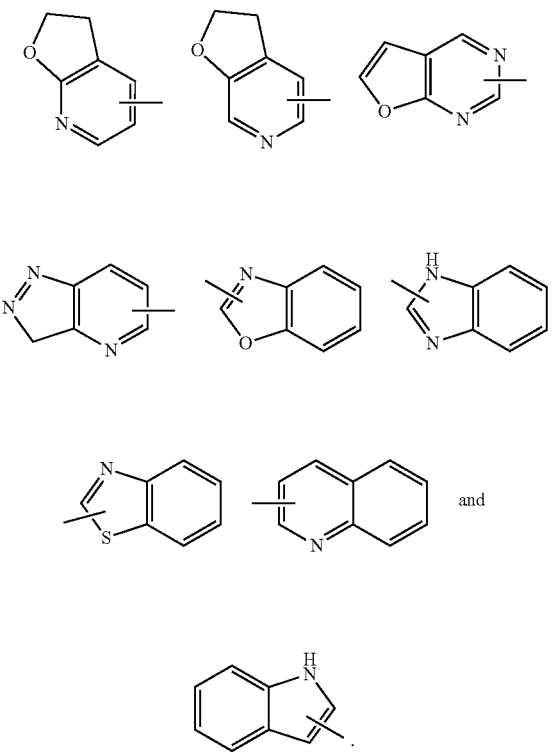

The heteroaryl can be optionally substituted or unsubstituted. When substituted, the substituent group(s) is preferably one or more groups independently selected from the group consisting of alkyl, alkenyl, alkynyl, alkoxyl, alkylthiol, alkylamino, halogen, thiol, hydroxyl, nitro, cyano, cycloalkyl, heterocyclyl, aryl, heteroaryl, cycloalkoxyl, heterocycloalkoxyl, cycloalkylthio, heterocyclylthio, carboxyl and carboxylate.

The term "alkoxyl" refers to an —O-(alkyl) or an —O-(unsubstituted cycloalkyl) group, wherein the alkyl is as defined above. Non-limiting examples of alkoxyl include methoxyl, ethoxyl, propoxyl, butoxyl, cyclopropoxyl, cyclobutoxyl, cyclopentyloxyl, cyclohexyloxyl. The alkoxyl can be optionally substituted or unsubstituted. When substituted, the substituent group(s) is preferably one or more groups independently selected from the group consisting of alkyl, alkenyl, alkynyl, alkoxyl, alkylthiol, alkylamino, halogen, thiol, hydroxyl, nitro, cyano, cycloalkyl, heterocyclyl, aryl, heteroaryl, cycloalkoxyl, heterocycloalkoxy, cycloalkylthio, heterocyclylthio, carboxyl or carboxylate.

The term "hydroxyalkyl" refers to an alkyl substituted by hydroxyl(s), wherein the alkyl is as defined above.

The term "haloalkyl" refers to an alkyl substituted by halogen(s), wherein the alkyl is as defined above.

The term "deuterated alkyl" refers to an alkyl substituted by deuterium atom(s), wherein the alkyl is as defined above.

The term "hydroxyl" refers to an —OH group.

The term "halogen" refers to fluorine, chlorine, bromine or iodine.

The term "amino" refers to —NH₂.

The term "cyano" refers to —CN.

The term "nitro" refers to —NO₂.

"Optional" or "optionally" means that the event or circumstance described subsequently can, butneed not to occur, and the description includes the situation in which the event or circumstance occurs or does not occur. For example, "the heterocyclyl optionally substituted by an alkyl" means that an alkyl can be, but need not to be present, and the description includes the situation in which the heterocyclyl is substituted by an alkyl and the heterocyclyl is not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical positions. Those skilled in the art are able to determine whether the substitution is possible or impossible by experiments or theory without excessive effort. For example, the binding of an amino or a hydroxyl having free hydrogen to a carbon atom having unsaturated bond (such as olefinic) may be unstable.

"Pharmaceutical composition" refers to a mixture comprising one or more of the compounds described herein, or a physiologically/pharmaceutically acceptable salt or a prodrug thereof, and other chemical components, as well as other components such as physiologically/pharmaceutically acceptable carriers and excipients. The purpose of the pharmaceutical composition is to facilitate administration of a compound to an organisms, which is conducive to the absorption of the active ingredient so as to show the biological activity.

The known starting materials in the present disclosure can be synthesized by or according to the methods known in the art, or can be purchased from Acros Organics or Aldrich Chemical Company and other companies, or can be obtained by the method described in CN102775401A.

The structures of the compounds are identified by nuclear magnetic resonance (NMR) and/or mass spectrometry (MS). NMR shift ($\delta$) is given in the unit of $10^{-6}$ (ppm). NMR is determined by a BrukerAVANCE-400 nuclear magnetic spectrometer. The solvents for determination are deuterated dimethyl sulfoxide (DMSO-d6), deuterated chloroform (CDCl$_3$) and deuterated methanol (CD$_3$OD), and the internal standard is tetramethylsilane (TMS). FINNIGANLCQAd (ESI) mass spectrometer (manufacturer: Thermo, model: FinniganLCQadvantageMAX) is used for ESI-MS determination. LCMS is determined by high performance liquid chromatography (manufacturer: Agilent, model: 1200) with gradient elution, positive ion scanning mode, and the quality scan range of 100~1500.

DESCRIPTION OF THE DRAWINGS

FIG. 1: Graph of the transformation trend of the compound of Example 5 in human plasma.

DETAILED DESCRIPTION

The present disclosure will be further described with reference to the following examples, but the examples should not be considered as limiting the scope of the present disclosure.

The experimental methods with unspecified conditions in the examples of the present disclosure generally follow conventional conditions, or according to the conditions recommended by the manufacturer of the raw material or product. The reagents with unspecified sources are conventional reagents purchased from the market.

Example 1

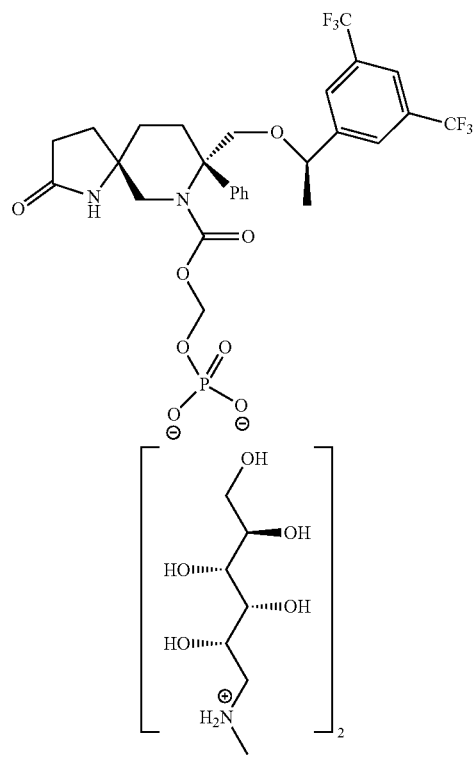

Step 1:

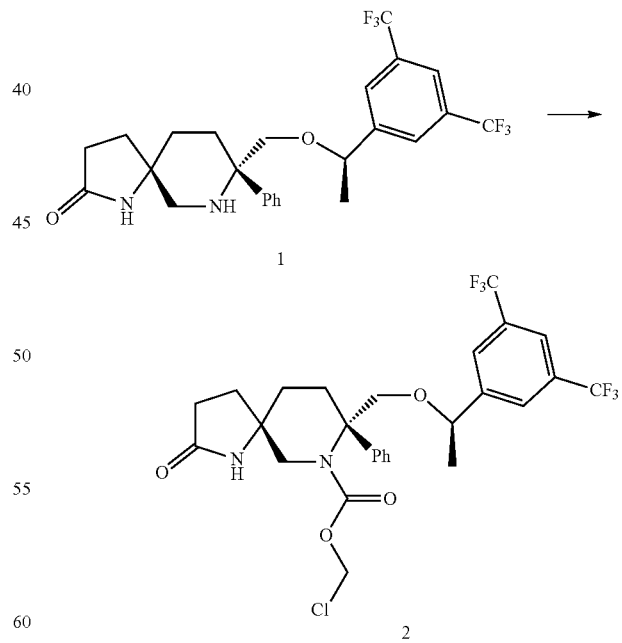

Compound 1 (2.43 g, 4.86 mmol, 1 eq) was weighed and dissolved in dichloromethane (36 mL) in a 100 mL three-necked flask under N$_2$ atmosphere. Diisopropylethylamine (5 g, 38.76 mmol, 8 eq) was added and the mixture was cooled to −30° C. Trimethylchlorosilane (1.36 g, 12.52 mmol, 2.6 eq) was added and the mixture was stirred at room temperature for 2 h. The reaction mixture was cooled to −25° C. A solution of chloromethyl chloroformate (0.77 g, 6 mmol, 1.23 eq) in dichloromethane was added dropwise and the mixture was stirred under controlled temperature at −20° C.~−5° C. until completion of the reaction. The reaction solution was poured into ice water, put to separation, and extracted with dichloromethane. Water and 1 N hydrochloric acid solution were added and put to separation. The organic layer was then successively washed with brine, saturated aqueous solution of sodium bicarbonate and brine, dried over anhydrous sodium sulfate, filtered and concentrated to give 3.0 g yellow jelly with a yield of 104%.

Step 2:

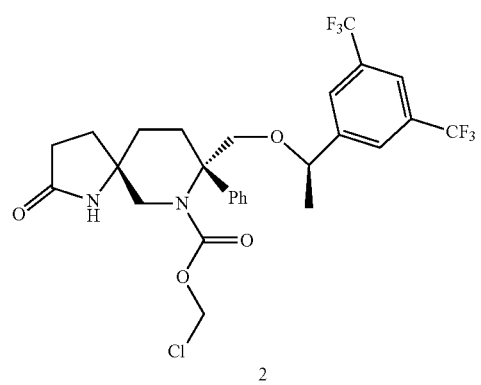

2

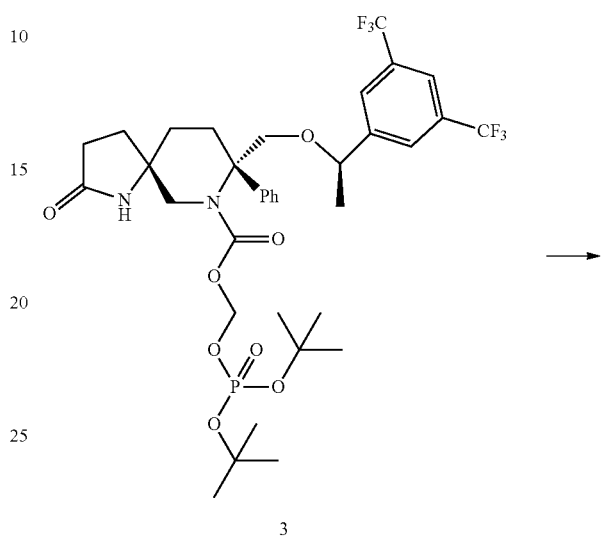

3

Compound 2 (2.8 g, 4.53 mmol, 1 eq), tetrabutylammonium iodide (1.68 g, 4.55 mmol, 1 eq), di-tert-butylphosphate potassium salt (5.63 g, 22.67 mmol, 5 eq) and dioxane (84 mL) were added into a 500 mL three-necked flask under $N_2$ atmosphere. The reaction mixture was heated to 55° C. and stirred for 4 h. The reaction solution was cooled, poured into ethyl acetate and water, put to separation, and extracted with ethyl acetate. The organic layer was washed with aqueous solution of sodium sulfite, and then successively washed with water and brine, dried over anhydrous sodium sulfate, filtered and concentrated to give 3.73 g yellow foam with a yield of 107%.

Step 3:

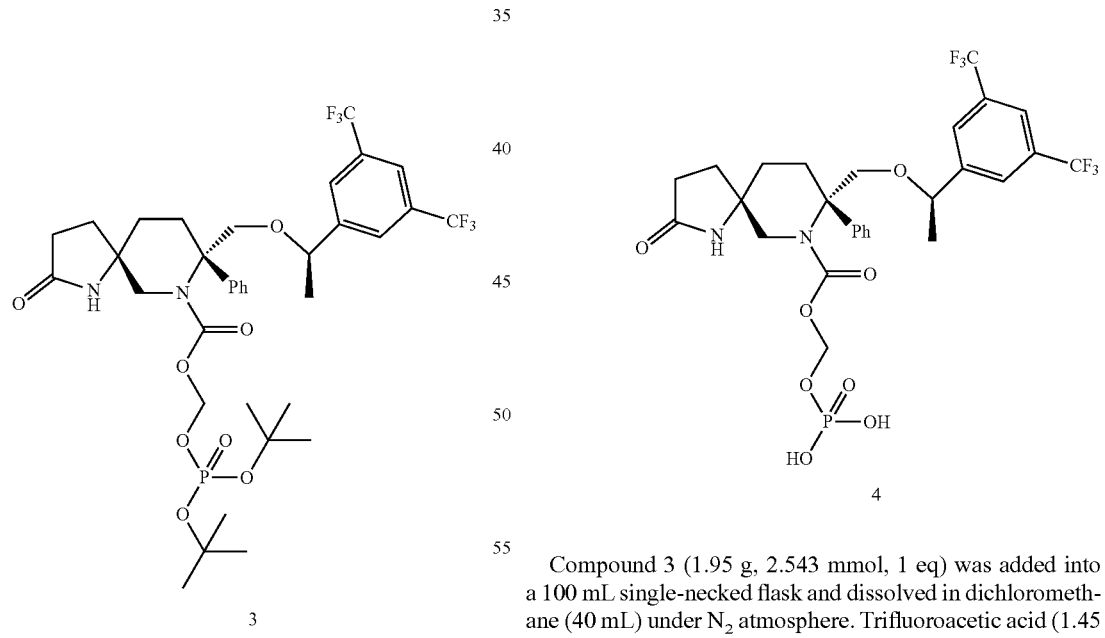

Compound 3 (1.95 g, 2.543 mmol, 1 eq) was added into a 100 mL single-necked flask and dissolved in dichloromethane (40 mL) under $N_2$ atmosphere. Trifluoroacetic acid (1.45 mL, 19.52 mmol, 8 eq) was added slowly under ice water cooling. The reaction mixture was stirred until completion of the reaction, and then concentrated to give 2.29 g oil which was then purified purified to give 1.39 g white foamy solid with a yield of 83.5%.

$^1$H-NMR (400 MHz, $CD_3OD$): δ(ppm) 7.89 (s, 2H), 7.86 (s, 1H), 7.41-7.27 (m, 5H), 5.66 (d, J=12 Hz, 1H), 5.50-5.47 (m, 1H), 4.60 (d, J=8 Hz, 1H), 4.20-3.88 (m, 3H), 2.51-2.10 (m, 5H), 1.86-1.66 (m, 3H), 1.44-1.31 (m, 4H).

Step 4:
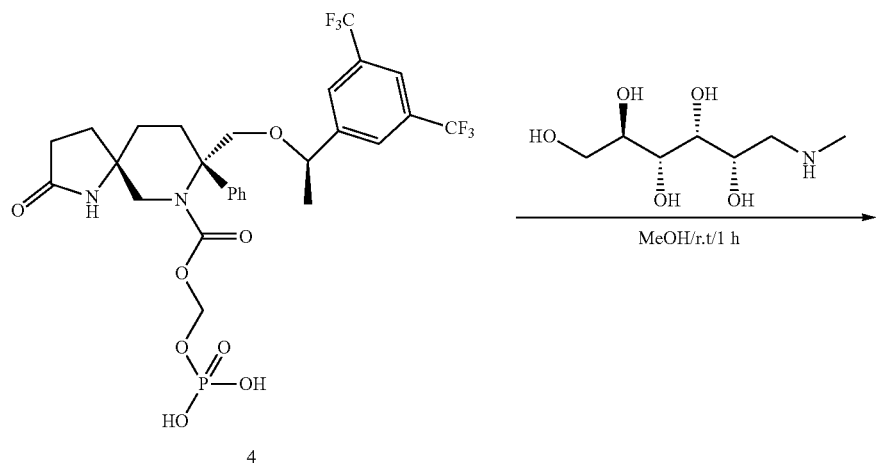
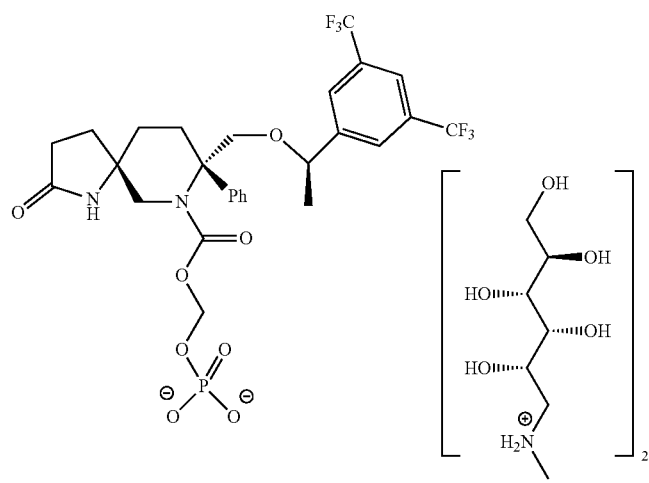

Compound 4 (111 mg, 0.17 mmol) and meglumine (59.6 mg, 0.305 mmol) were added to a 50 mL single-neck flask and dissolved in methanol (5 mL). The reaction mixture was stirred at room temperature for 1.5 h and then concentrated to give 174 mg white solid salt.

Example 2

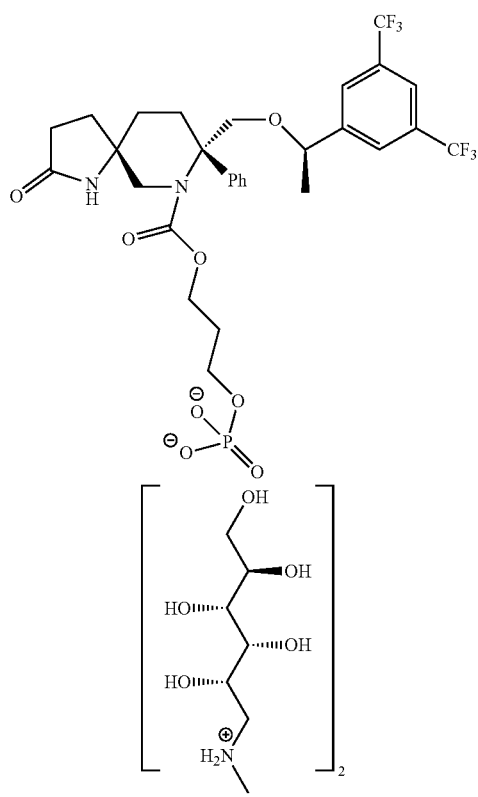

Step 1:

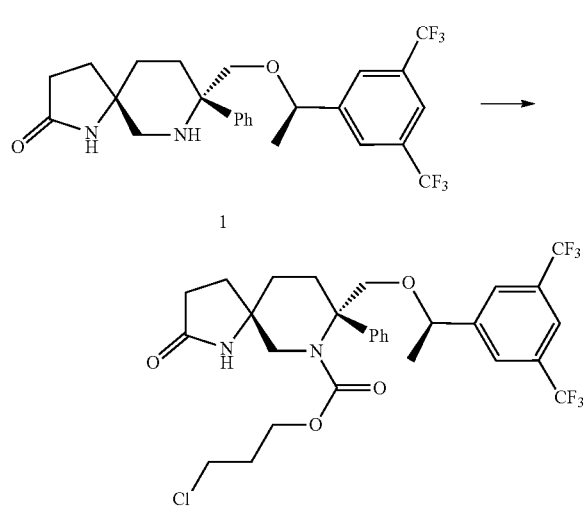

Compound 1 (5 g, 10 mmol, 1 eq) was placed in a 250 mL three-neck flask and 50 mL of dichloromethane was added. The reaction mixture was replaced with $N_2$. Diisopropylethylamine (5.1 g, 40 mmol, 4 eq) was added and the mixture was cooled to 0° C. 3-Chloropropyl chloroformate (4.71 g, 30 mmol, 3 eq) was added slowly dropwise and the reaction mixture was stirred until completion of the reaction. The reaction solution was washed with 20 mL×2 water, dried over anhydrous sodium sulfate and concentrated. The crude product was pulped with 20 mL of tert-butyl methyl ether, filtered and dried to give 5.3 g product as a white solid, with a yield of 85.5% and a HPLC purity of 95.2%.

Step 2:

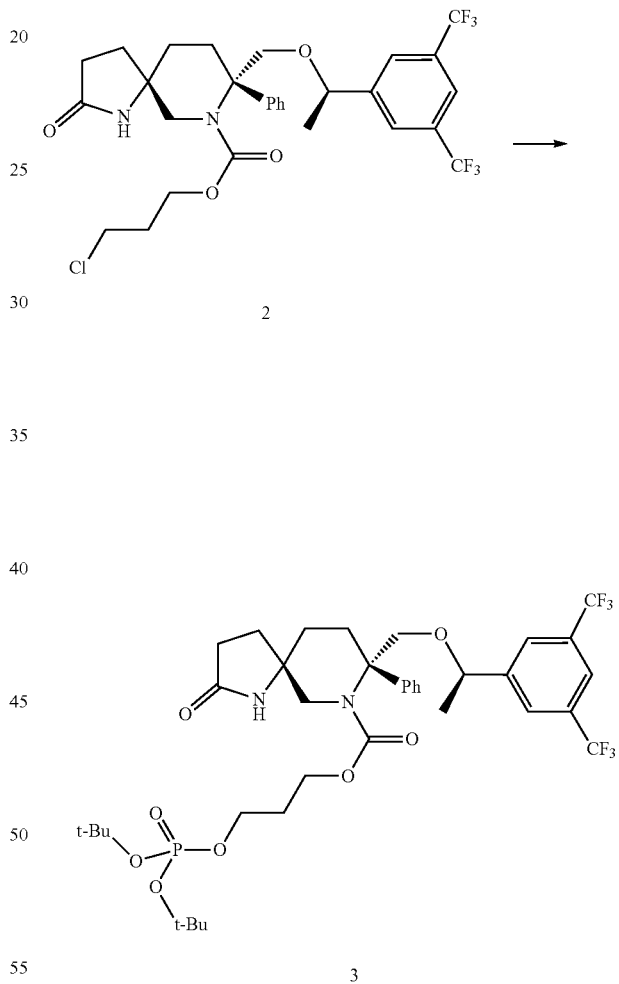

Compound 2 (500 mg, 0.833 mmol, 1 eq) was placed in a 25 mL round bottom flask. 5 mL of dimethylformamide, 5 mg potassium iodide and di-tert-butyl phosphate tetrabutyl quaternary ammonium (564 mg, 1.25 mmol, 1.5 eq) were added. The temperature was raised to 100° C. until completion of the reaction. The reaction mixture was concentrated and the residues were purified by HPLC to give 370 mg product with a yield of 57.8% and a HPLC purity of 97%.

Step 3:

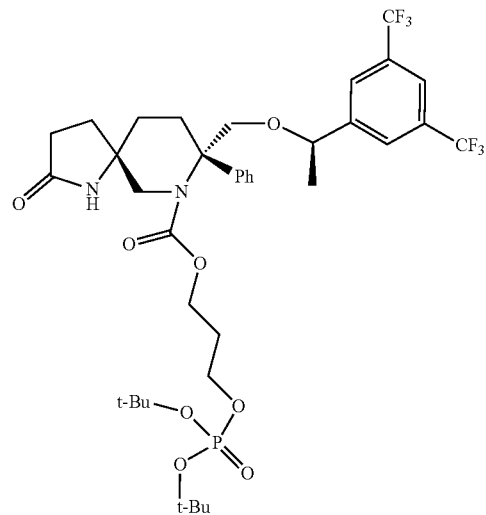
3

Compound 3 (2 g, 2.52 mmol) was dissolved in a solution of hydrochloric acid in dioxane (25 mL, 4 M), and stirred at room temperature for 30 minutes. The reaction mixture was evaporated to dry under reduced pressure to give compound 4 (1.4 g, 2.05 mmol) with a yield of 81%.

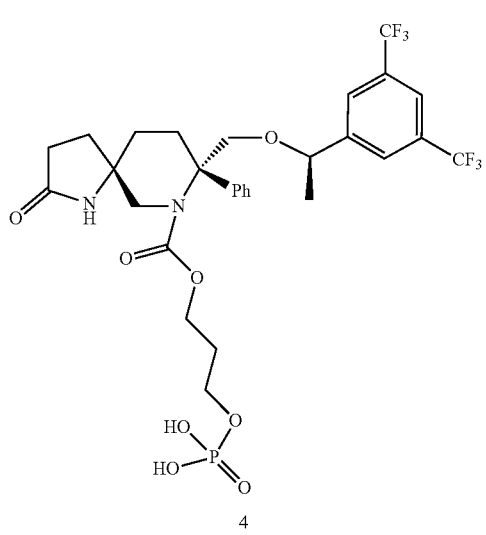
4

Step 4:

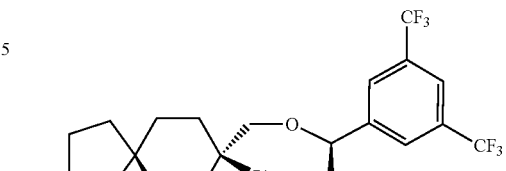
4

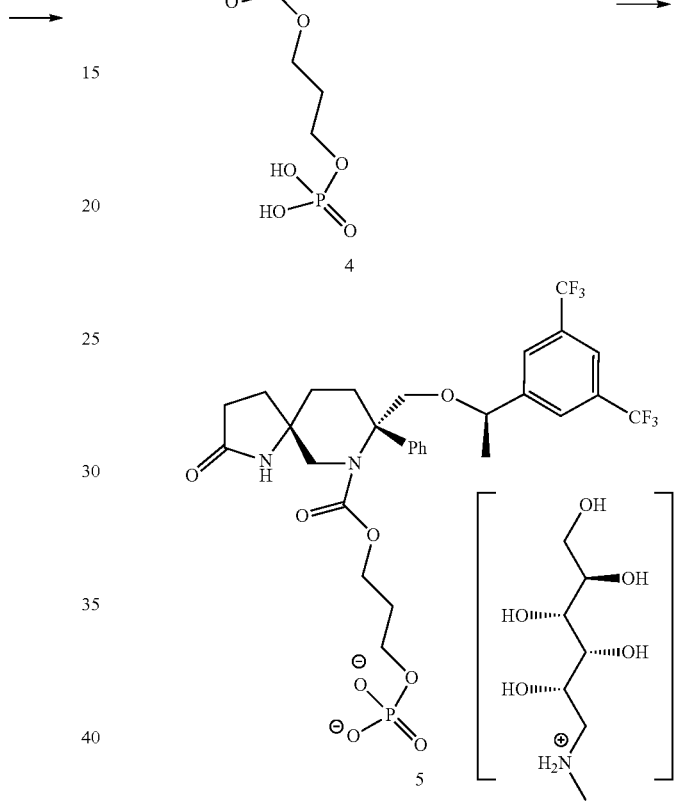
5

Compound 4 (700 mg, 1.025 mmol) and meglumine (310 mg, 2 mmol) were dissolved in methanol (10 mL) at 25° C. and stirred for 1 h. The reaction mixture was concentrated under reduced pressure to give a crude product of compound 5 (1.1 g), which was then pulped with methyl tert-butyl ether and filtered and then dried to give the pure product of compound 5 (1 g, 0.932 mmol) with a yield of 91%.

$^1$H-NMR (400 MHz, CD$_3$OD): δ7.90-7.84 (m, 3H), 7.32-7.25 (m, 5H), 4.14-3.61 (m, 25H), 2.81 (m, 5H), 2.47-2.29 (m, 12H), 1.79-1.63 (m, 5H), 1.46-1.29 (m, 3H), 1.21-1.12 (m, 6H).

Example 3

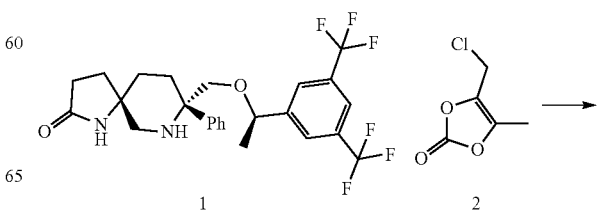
1        2

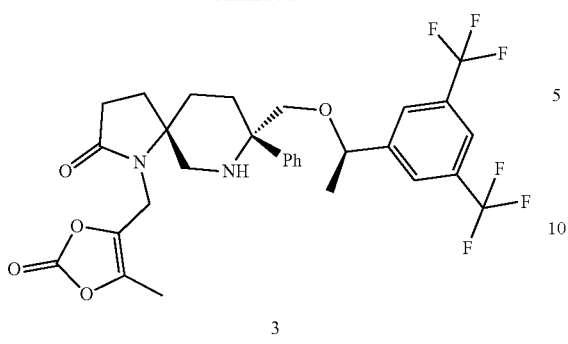

3

2 ml of acetone and 100 mg compound 1 were added into a 25 ml flask and stirred. Potassium carbonate (42 mg, 0.3 mmol, 1.5 eq) was added in batches and the mixture was stirred at room temperature for half an hour. 36 mg compound 2 was added to the reaction flask. The reaction mixture was stirred at room temperature for about 18 hours until completion of the reaction, and purified by column chromatography to give 50 mg 3 (yield 40.8%).

$^1$H-NMR (400 MHz, CDCl$_3$): δ=7.79 (s, 1H), 7.72 (s, 2H), 7.42-7.40 (d, J=8 Hz, 2H), 7.31-7.27 (m, 2H), 7.27-7.21 (m, 1H), 5.58 (s, 1H), 4.55-4.53 (m, 1H), 4.06-3.99 (m, 2H), 3.69-3.67 (d, J=8 Hz, 1H), 3.53-3.49 (d, J=16 Hz, 1H), 3.25-3.21 (d, J=16 Hz, 1H), 2.77-2.74 (d, J=12 Hz, 1H), 2.59-2.57 (d, J=8 Hz, 1H), 2.34-2.31 (m, 3H), 1.97-1.71 (m, 7H), 1.46-1.45 (d, J=4 Hz, 3H).

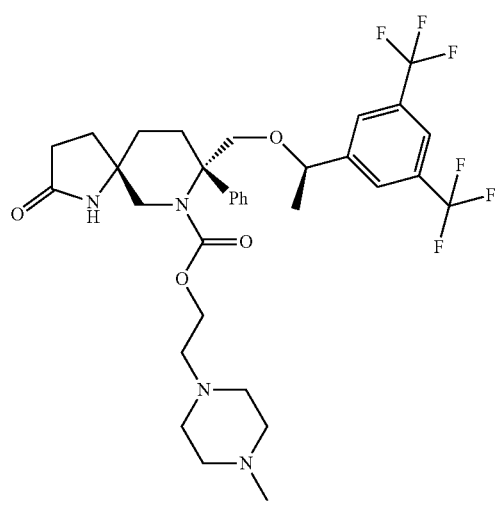 [SMILES: C[C@@H](OC[C@@]1(c2ccccc2)CC[C@]2(CCC(=O)N2)CN1C(=O)OCCN1CCN(C)CC1)c1cc(C(F)(F)F)cc(C(F)(F)F)c1]

Example 4

Step 1:

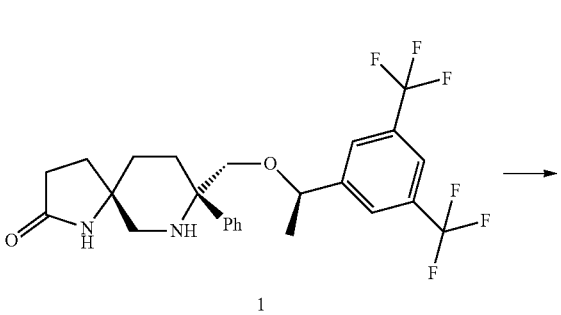

1

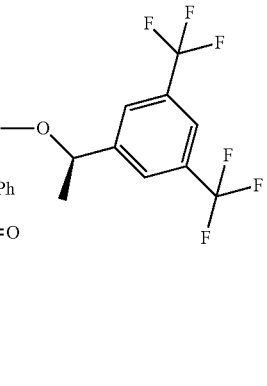

2

750 mg compound 1 and 2.1 ml of diisopropylethylamine were added into a three-necked flask under nitrogen atmosphere. Then 12 ml of anhydrous dichloromethane was added. The mixture was cooled to −40° C. and 0.5 ml of trimethylchlorosilane was added dropwise. The mixture was stirred at room temperature for two hours. Then the reaction mixture was cooled to −30° C. to −20° C. and 0.024 ml of chloroethyl chloroformate dissolving in 3 ml of anhydrous dichloromethane was added dropwise. The reaction mixture was stirred at −20° C. to 5° C. until completion of the reaction. The reaction was quenched by adding water. The liquid was put to separation and washed successively with 1 N diluted hydrochloric acid, saturated brine, saturated aqueous solution of sodium bicarbonate and saturated brine. The organic layer was dried over anhydrous sodium sulfate and filtered. The filtrate was concentrated under reduced pressure and dried under vacuum to give 1 g 2 as white solid.

Step 2:

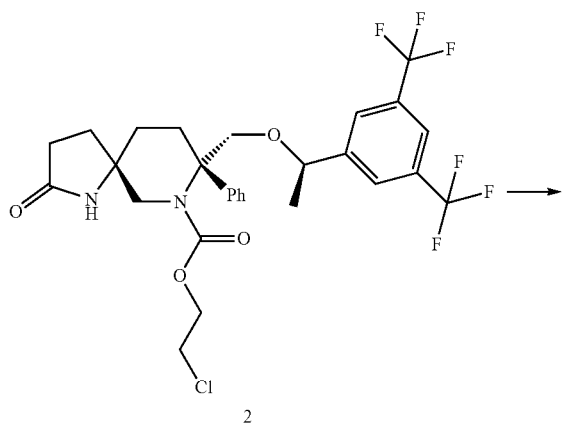

Example 5

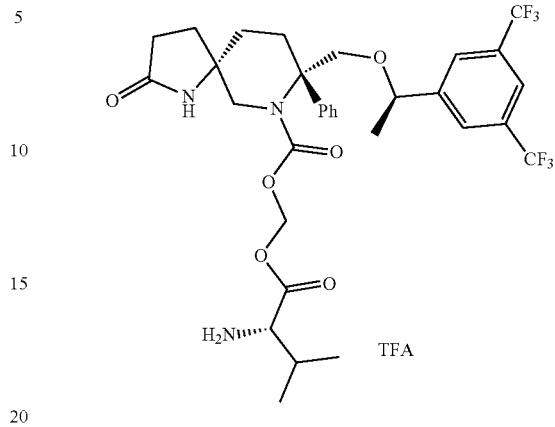

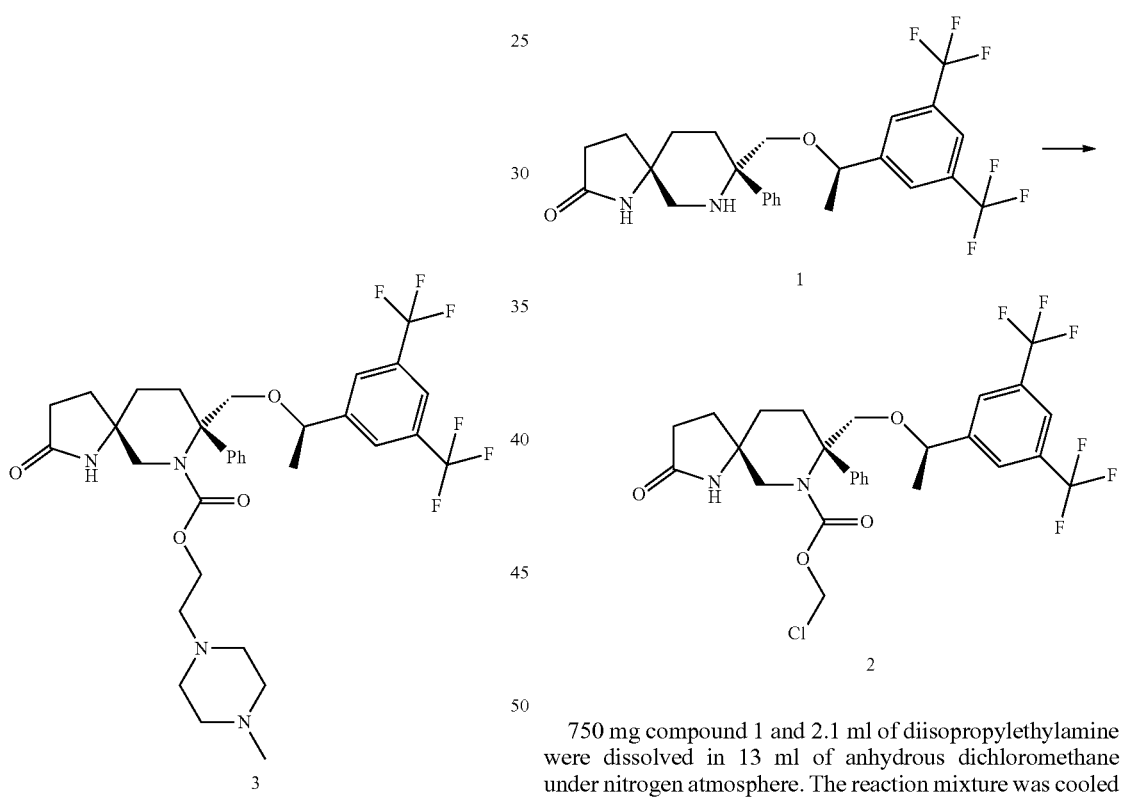

1 g compound 2 and 0.99 g sodium iodide were dissolved in 10 ml of dimethylformamide. 1.15 ml of diisopropylethylamine and 0.75 ml of methylpiperazine were added. The reaction mixture was heated to 90° C. and stirred until completion of the reaction. The reaction solution was directly concentrated and the residues were purified by HPLC to give 430 mg compound 3.

$^1$H-NMR (400 MHz, CDCl$_3$): δ7.77 (s, 1H), 7.73 (s, 2H), 7.37-7.26 (m, 5H), 6.56 (s, 1H), 4.44-4.40 (m, 1H), 4.29-4.24 (m, 2H), 4.10-4.07 (m, 1H), 3.90-3.87 (d, J=12 Hz, 1H), 3.79-3.76 (d, J=12 Hz, 1H), 3.01-2.97 (d, J=16 Hz, 1H), 2.52-2.32 (m, 15H), 1.93-1.65 (m, 6H), 1.29-1.28 (d, J=4 Hz, 3H).

750 mg compound 1 and 2.1 ml of diisopropylethylamine were dissolved in 13 ml of anhydrous dichloromethane under nitrogen atmosphere. The reaction mixture was cooled to −10° C. and 0.5 ml of trimethylchlorosilane was added dropwise. The mixture was then warmed to room temperature and stirred for three hours. The mixture was cooled to −10° C. again And 3 ml of solution of chloromethyl chloroformate (0.288 g) in dichloromethane was added. The reaction mixture was then reacted at −10° C. until completion of the reaction. The reaction was quenched by water. The liquid was put to separation and washed successively with diluted hydrochloric acid, saturated brine, saturated aqueous solution of sodium bicarbonate and saturated brine. The organic layer was dried over anhydrous sodium sulfate and filtered. The filtrate was concentrated under reduced pressure and the residues were purified to give 400 mg compound 2 as a white solid.

Step 2:

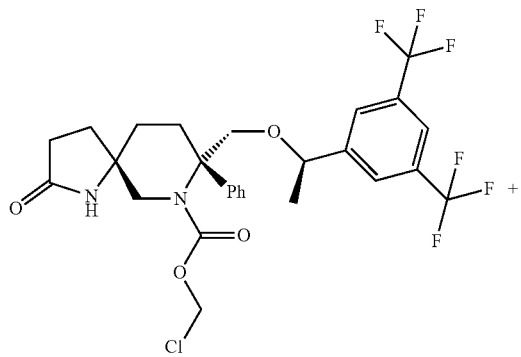

2

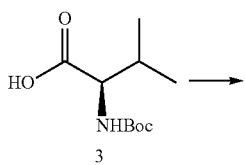

3

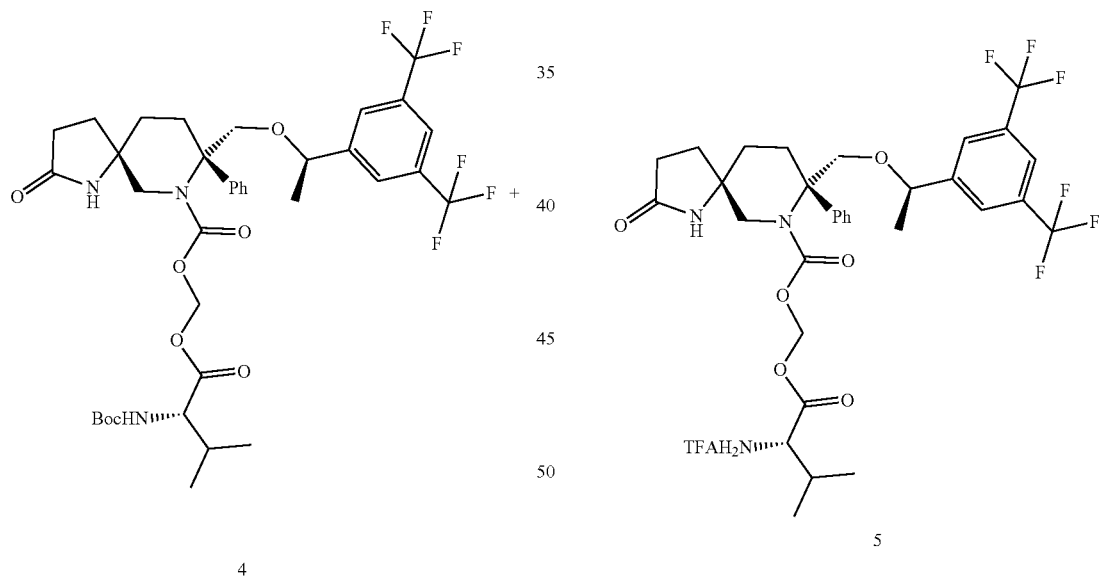

4

Step 3:

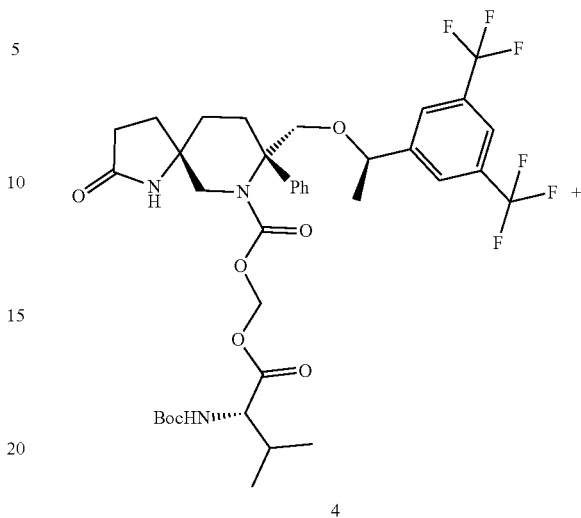

147 mg compound 3 and 203 mg sodium iodide were added to 2 ml of dimethylformamide, followed by addition of 136 mg potassium bicarbonate. The reaction mixture was stirred at room temperature for half an hour, and then 400 mg compound 2 dissolving in 10 ml of dimethylformamide was added dropwise. The mixture was reacted overnight. The reaction was quenched by adding water. The reaction mixture was extracted twice with ethyl acetate. The organic phases were collected, dried over anhydrous sodium sulfate, filtered and concentrated. The concentrate was purified by silica gel column to give 450 mg compound 4 as an oil.

405 mg compound 4 was dissolved in 18 ml of dichloromethane. 4.5 ml of trifluoroacetic acid was added dropwise under cooling in an ice bath. After addition, the reaction was warmed to room temperature and stirred for two hours. The reaction mixture was concentrated and the residues were purified by column chromatography to give 330 mg of product, compound 5, with a yield of 80%.

$^1$H-NMR (400 MHz, CDCl$_3$): δ 8.34 (s, 1H), 7.72 (s, 1H), 7.63 (s, 2H), 7.40-7.28 (m, 5H), 6.19 (s, 1H), 5.68-5.67 (d, J=4 Hz, 1H), 4.30-4.29 (d, J=4 Hz, 1H), 4.20-4.17 (d, J=12 Hz, 1H), 3.99-3.91 (m, 2H), 3.79 (s, 1H), 2.70-2.67 (d, J=12 Hz, 1H), 2.49-2.21 (m, 8H), 1.83-1.70 (m, 4H), 1.29-1.28 (m, 3H), 1.09-1.07 (m, 6H).

Example 6

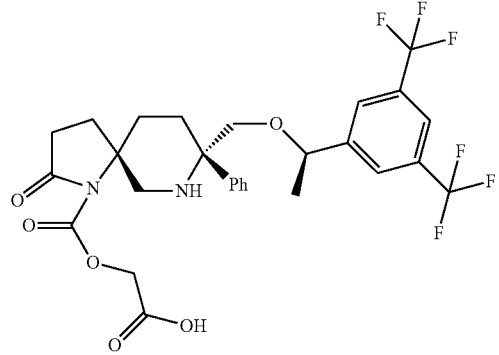 [SMILES: C[C@@H](OC[C@@]1(c2ccccc2)CC[C@]2(CCC(=O)N2C(=O)OCC(=O)O)CN1)c1cc(C(F)(F)F)cc(C(F)(F)F)c1]

Step 1:

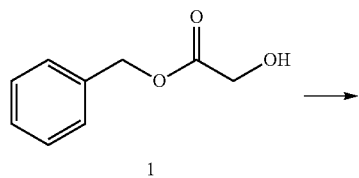

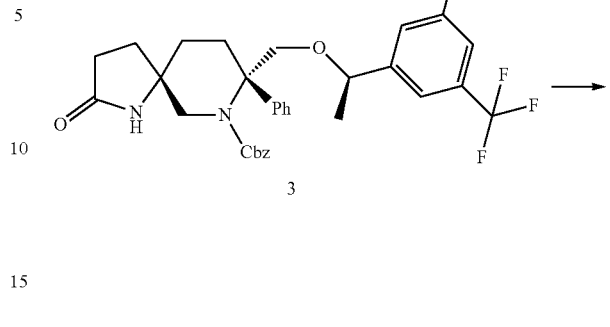

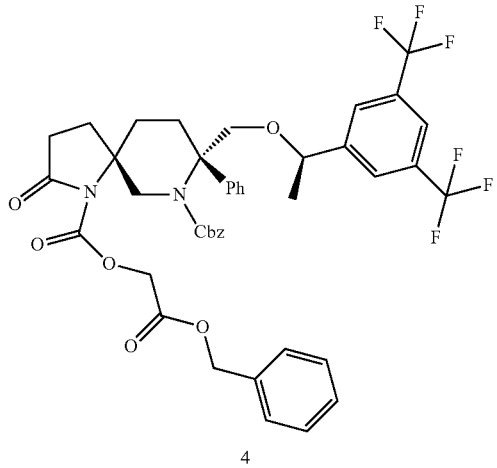

1.294 g triphosgene was dissolved in 7.5 ml of anhydrous tetrahydrofuran. The solution was cooled in an ice bath and replaced with nitrogen for three times. Then 0.33 ml of pyridine was added dropwise. After addition, a solution of 500 mg compound 1 dissolving in 7.5 ml of anhydrous tetrahydrofuran was added dropwise. After addition, the reaction was stirred at 5° C. for 3 hours. 30 ml of dichloromethane was added for dilution. The solution was washed successively with diluted hydrochloric acid, water and saturated brine, dried over anhydrous sodium sulfate, filtered and concentrated to give 700 mg crude product.

Step 2:

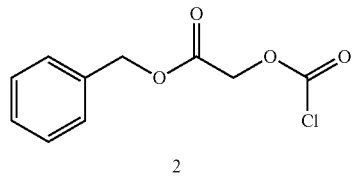

128 mg compound 3 was added to 2 ml of anhydrous tetrahydrofuran. The reaction mixture was replaced with nitrogen for three times. The reaction was cooled to about −65° C., and 0.28 ml of lithium hexamethyldisilazide (1 mol/L, dissolving in n-hexane) was added dropwise. The mixture was stirred for half an hour. Meanwhile, 60 mg crude product of compound 2 from the previous step was dissolved in 1 ml of anhydrous tetrahydrofuran. The mixture was cooled to −65° C. after replacing with nitrogen for three times. The lithium salt of compound 3 prepared above was transferred into the reaction flask containing acyl chloride compound 2. After addition, the reaction was completed at −65° C. and quenched by adding saturated aqueous solution of ammonium chloride. The reaction mixture was extracted with ethyl acetate. The organic phase was concentrated and directly purified by column chromatography to give 62 mg compound 4.

Step 3:

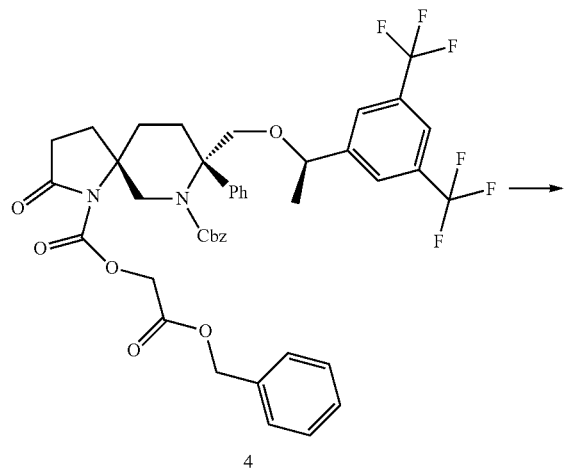

4

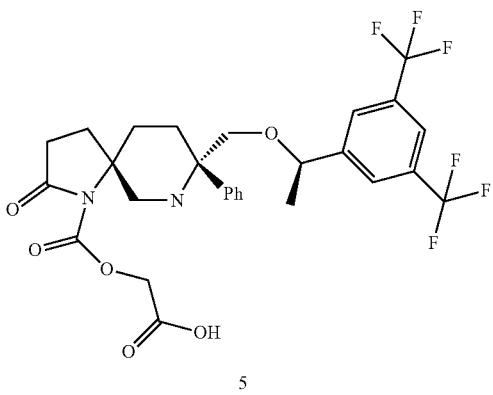

5

62 mg compound 4 and 31 mg of 20% wet palladium hydroxide were added to 1.5 ml of ethyl acetate and stirring was started. The reaction mixture was replaced with hydrogen for three times, stirred at room temperature for 5 hours and filtered. The filter cake was washed with ethyl acetate. The filtrate was concentrated and the residues were purified to give 41 mg of compound 5 as a white solid.

$^1$H-NMR (400 MHz, CDCl$_3$) δ=7.72 (s, 1H), 7.57 (s, 2H), 7.50-7.41 (m, 5H), 4.80-4.59 (m, 3H), 4.17-4.13 (d, J=16 Hz, 1H), 3.83-3.80 (d, J=12 Hz, 1H), 3.62-3.59 (d, J=12 Hz, 1H), 3.26-3.22 (d, J=16 Hz, 1H), 2.60-2.47 (m, 4H), 2.26-2.18 (m, 2H), 1.85-1.80 (m, 2H), 1.45-1.43 (d, J=8 Hz, 3H), 0.89-0.83 (m, 1H).

Example 7

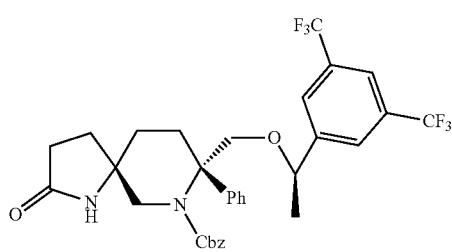

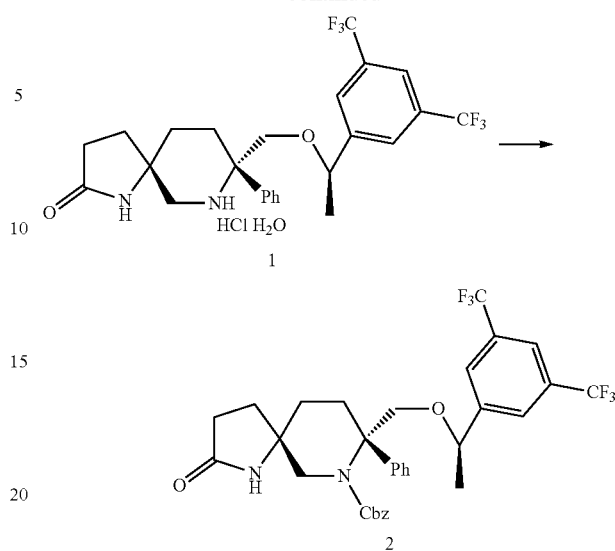

Potassium carbonate (11.7 g, 84.66 mmol, 8.47 eq) was dissolved in water (40 mL) until use. Compound 1 (5.55 g, 10 mmol, 1 eq) was suspended in ethyl acetate (80 mL) under N$_2$ atmosphere, to which the aforementioned aqueous solution of potassium carbonate was added under cooling by an ice-bath. The reaction solution gradually became clear under stirring, and then Cbz-Cl (1.7 mL, 12 mmol, 1.2 eq) was added dropwise. After addition, the reaction mixture was stirred for 10 min, and stirred at room temperature overnight. The reaction solution was put to separation and extracted with ethyl acetate. The organic phases were collected, dried over anhydrous sodium sulfate, filtered and concentrated. The residues were purified by column chromatography to give 4.3 g white solid with a yield of 56%.

Example 8

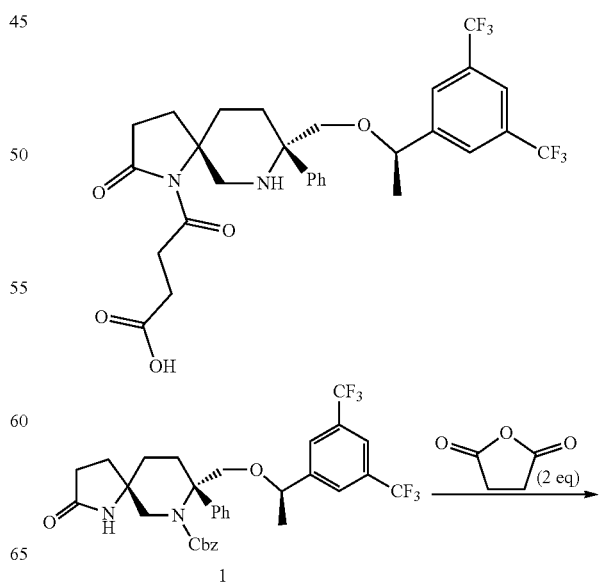

-continued

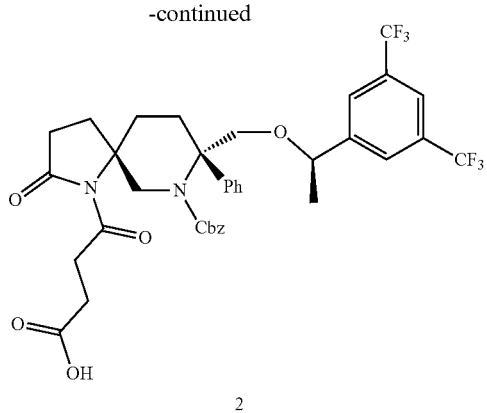

2

Compound 1 (317 mg, 0.5 mmol) and THF (7.2 mL) were added into a 50 ml of single-necked flask under nitrogen atmosphere and then stirred to dissolve and cooled to −20° C. NaHMDS (2 M, 0.5 mL, 1 mmol) was added dropwise and the reaction mixture was stirred until completion of the reaction. The reaction was quenched by saturated ammonium chloride. The reaction mixture was extracted with methyl tert-butyl ether. The organic layer was washed with saturated brine, dried over anhydrous sodium sulfate and concentrated. The residues were purified by column chromatography to give compound 2 (250 mg) with a yield of 68%.

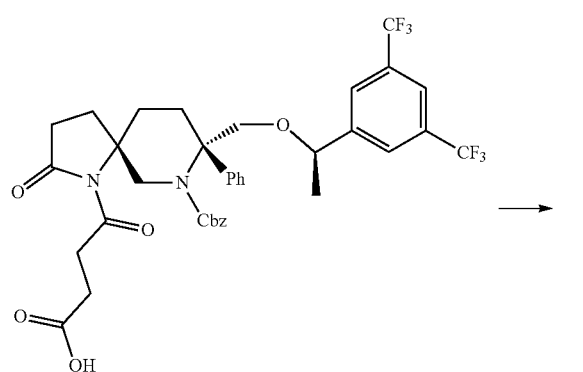

2

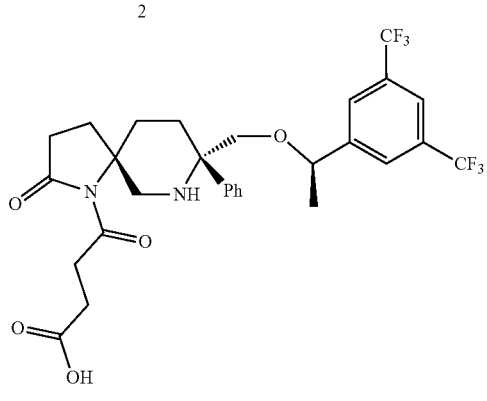

3

Compound 2 (250 mg, 0.34 mmol), methanol (10 mL) and palladium on carbon (10%, 250 mg) were added into a 50 ml of single-neck flask. The reaction mixture was stirred at room temperature under hydrogen atmosphere until comple-tion of the reaction. The reaction mixture was filtered and the residues were concentrated to give compound 3 (150 mg) with 74% yield.

LCMS: 601 [M+1].

Example 9

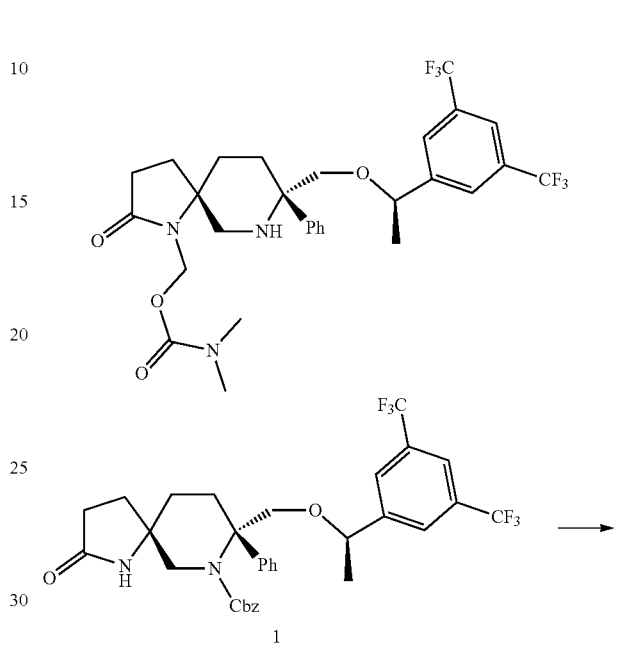

Compound 1 (215 mg, 0.339 mmol, 1 eq), anhydrous potassium carbonate (55 mg, 0.396 mmol, 1.1 eq), paraformaldehyde (37 mg, 1.23 mmol, 3.3 eq) and THF (5 ml) were added into a 50 mL reaction flask under $N_2$ atmosphere. The reaction mixture was heated and stirred until completion of the reaction. The reaction mixture was filtered and concentrated to give a crude product, which was purified by column chromatography to give 216 mg of oil 2 with a yield of 95%.

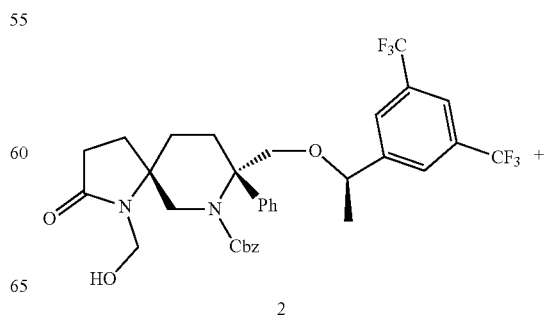

2

-continued

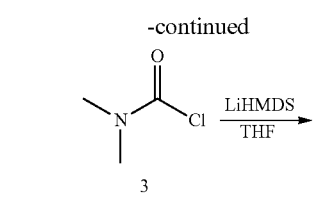

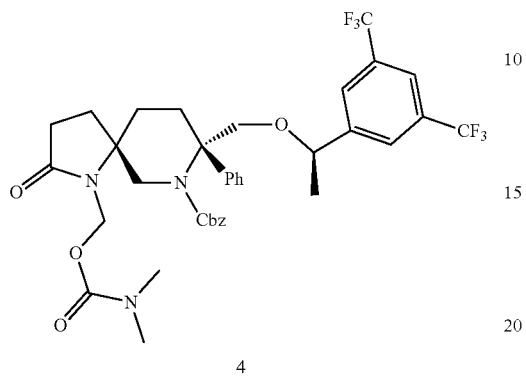

Compound 2 (66 mg, 0.1 mmol, 1 eq) and THF (5 ml) were added to a reaction flask under N₂ atmosphere. LiHMDS (1 M in THF, 0.2 ml, 0.2 mmol, 2 eq) and then compound 3 (40 mg, 0.37 mmol, 3.7 eq) were added dropwise and the reaction mixture was stirred until completion of the reaction. The reaction mixture was extracted with ethyl acetate and concentrated to give a crude product, which was purified by column chromatography to give 27 mg of crude product 4 as an oil with a yield of 36%.

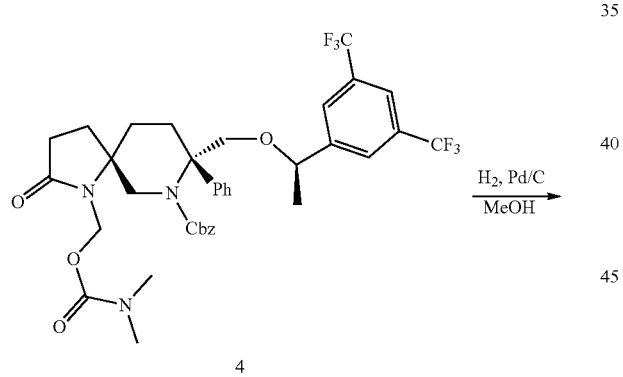

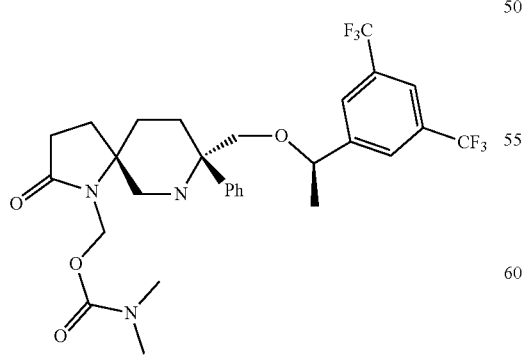

Compound 4 (27 mg, 0.367 mmol, 1 eq), Pd/C (33 mg) and methanol (5 ml) were added to a reaction flask at room temperature, and stirred under hydrogen atmosphere until completion of the reaction. The reaction mixture was filtered and concentrated to give a crude product, which was subjected to column chromatography to give 13 mg of oil 5 with a yield of 58.8%.

LCMS: 602 [M+1].

Example 10

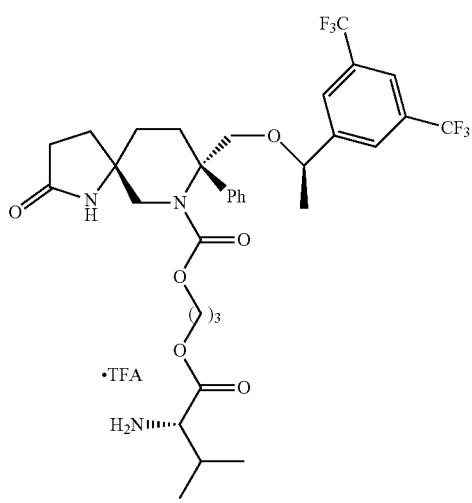

The target compound was synthesized according to the method of Example 5 with replacing chloromethyl chloroformate by chloropropyl chloroformate. LCMS: 702 [M+1].

Example 11

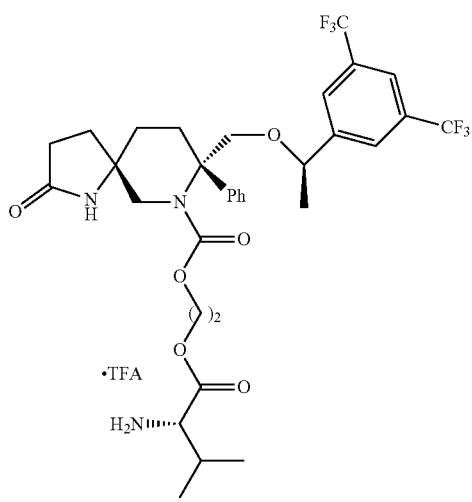

The target compound was synthesized according to the method of Example 5 with replacing chloromethyl chloroformate by chloroethyl chloroformate. LCMS: 688 [M+1].

Example 12

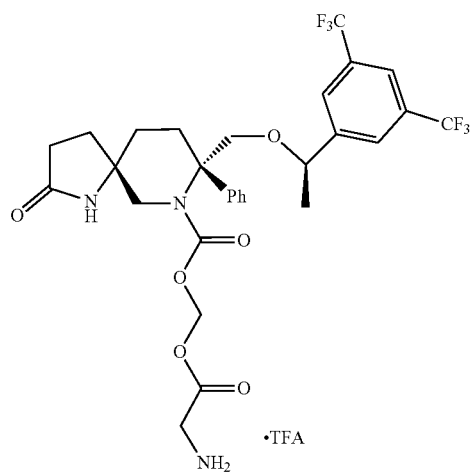 [SMILES: C[C@@H](OC[C@@]1(c2ccccc2)CC[C@]2(CCC(=O)N2)CN1C(=O)OCOC(=O)CN)c1cc(C(F)(F)F)cc(C(F)(F)F)c1]

The target compound was synthesized according to the method of Example 5 with replacing Boc-L-valine by N-Boc-glycine. LCMS: 632 [M+1].

Example 13

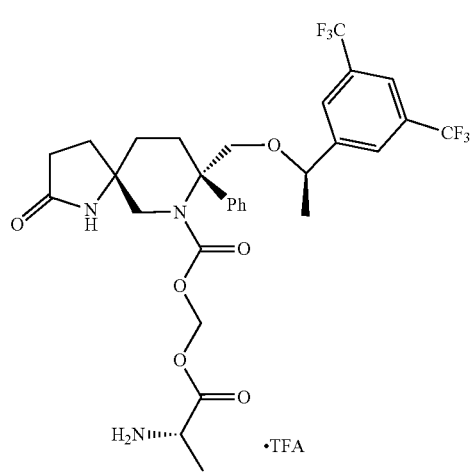 [SMILES: C[C@H](N)C(=O)OCOC(=O)N1C[C@@]2(CCC(=O)N2)CC[C@@]1(CO[C@H](C)c1cc(C(F)(F)F)cc(C(F)(F)F)c1)c1ccccc1]

The target compound was synthesized according to the method of Example 5 with replacing Boc-L-valine by Boc-L-alanine. LCMS: 646 [M+1].

Example 14

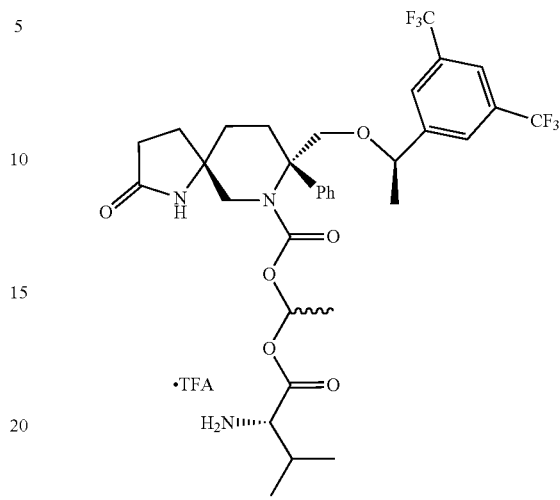

The target compound (isomers approximately 1/1) was synthesized according to the method of Example 5 with replacing chloromethyl chloroformate by 1-chloroethyl chloroformate. LCMS: 688 [M+1].

Example 15

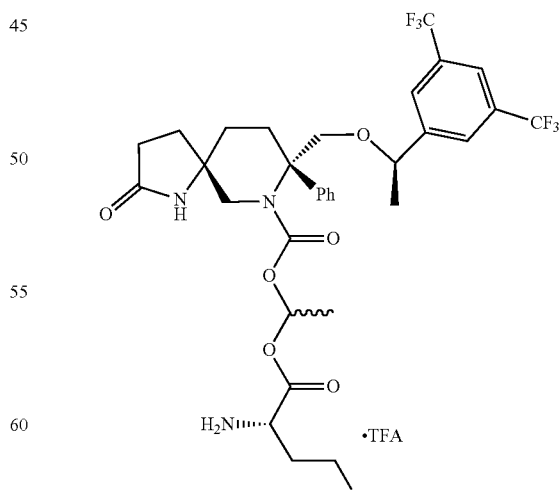

The target compound was synthesized according to the method of Example 5 with replacing Boc-L-valine by Boc-L-methionine. LCMS: 706 [M+1].

Example 16

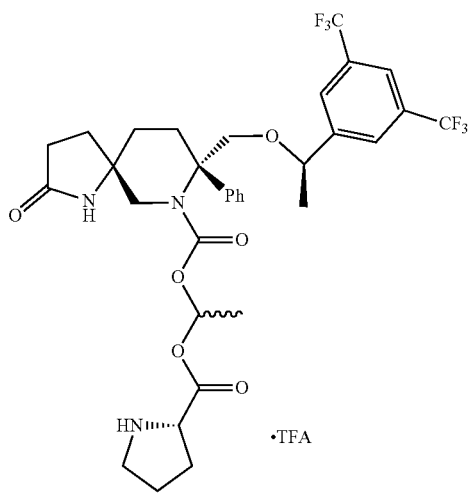 [SMILES: CC(OC(=O)[C@@H]1CCCN1)OC(=O)N1C[C@@]2(CCC(=O)N2)CC[C@@]1(CO[C@H](C)c1cc(C(F)(F)F)cc(C(F)(F)F)c1)c1ccccc1]

The target compound was synthesized according to the method of Example 5 with replacing Boc-L-valine by Boc-L-proline. LCMS: 672 [M+1].

Example 17

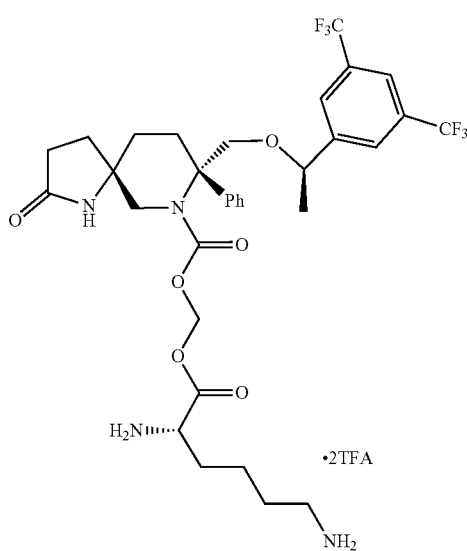 [SMILES: C[C@@H](OC[C@@]1(c2ccccc2)CC[C@]2(CCC(=O)N2)CN1C(=O)OCOC(=O)[C@@H](N)CCCCN)c1cc(C(F)(F)F)cc(C(F)(F)F)c1]

The target compound was synthesized according to the method of Example 5 with replacing Boc-L-valine by (S)-2,6-di-tert-butylcarbonylaminocaproic acid. LCMS: 703 [M+1].

Example 18

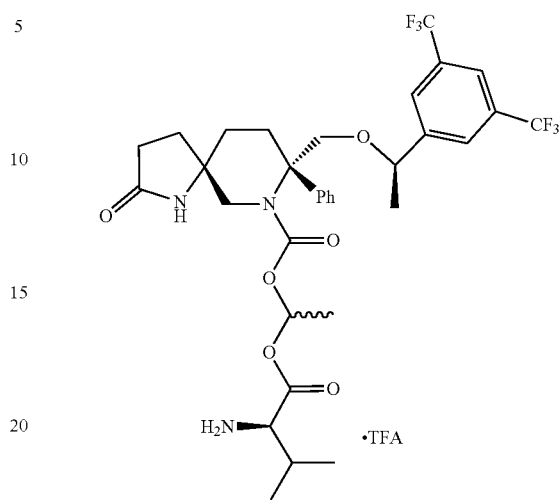

The target compound was synthesized according to the method of Example 5 with replacing Boc-L-valine by Boc-D-valine. LCMS: 674 [M+1].

Test Example 1: Water Solubility Data and Chemical Stability 1.1. Preparation of Reagents
Reagent: $NaH_2PO_4 \cdot 2H_2O$
1.2. Preparation Method
The 100 mL strength reagents were prepared as follows:
pH=3.0: phosphate buffer solution: 100 ml of 20 mmol/L $NaH_2PO_4$, 0.1M $H_3PO_4$, adjusting pH to 3.0.
pH=4.0: phosphate buffer solution: 100 ml of 20 mmol/L $NaH_2PO_4$, 0.1M $H_3PO_4$, adjusting pH to 4.0.
pH=7.0: ultrapure water
pH=9.0: phosphate buffer solution: 100 ml of 20 mmol/L $Na_2HPO_4$, 0.1M NaOH solution, adjusting pH to 9.0.
1.3. Test Method
An appropriate amount of test compound was accurately weighed. The solution was added at a small amount each time for several times and stirred until the compound was dissolved, and the content of the compound in the solution was determined. The data are shown in Table 1.
2.1 Test of Stability of the Compounds
About 1 mg of sample was weighed into a vial, then the vial was placed in a vacuum bag and the bag was vacuumized. Then the bag was put into a container containing color-changing silica gel and sealed. Two parallel samples were prepared. Enough samples were prepared according to the sampling time point and placed at 4° C. and room temperature respectively. The data are shown in Table 1.

TABLE 1

| No. | Water solubility | Chemical stability |
|---|---|---|
| Example 1 | >10 mg/ml (PH = 5) | Good |
| Example 2 | 9.05 mg/ml (PH = 5) | Good |
| Example 3 | <0.1 mg/ml (PH = 5) | Good |
| Example 4 | 2.08 mg/mL (PH = 3) | Good |
| Example 5 | >10 mg/ml (PH = 4) | Good |
| Example 6 | 1.12 mg/ml (PH = 3) | Good |
| Example 7 | NA | NA |

TABLE 1-continued

| No. | Water solubility | Chemical stability |
|---|---|---|
| Example 8 | 1.37 mg/ml (PH = 5) | Moderate |
| Example 9 | <0.1 mg/ml (PH = 3) | Good |
| Example 10 | 1.86 mg/mL(PH = 3) | |
| Example 11 | 2.81 mg/mL(PH = 3) | Good |
| Example 12 | NA | Poor |
| Example 13 | NA | Moderate |
| Example 14 | 4.5 mg/ml (PH = 4) | Good |
| Example 15 | NA | Poor |
| Example 16 | NA | Poor |
| Example 17 | NA | Moderate |
| Example 18 | 2.62 mg/mL (PH = 4) | Good |

Note:
Good: purity reduced by <0.5% after placing for 7 days;
Moderate: purity reduced by 0.5%~2.0% after placing for 7 days;
Poor: purity reduced by >2.0% after placing for 7 days.

Test Example 2: Plasma Stability Test

Test Protocol
1.1 Test Drug
The compound of Example 5 and the compound of formula I.
1.2 Test Plasma
Human fresh plasma was donated by volunteers with informed consent.
1.3 Preparation of Solution of the Compound
A certain amount of the compound of Example 5 was weighed and DMSO was added to prepare a 30 mM stock solution. A certain volume of the stock solution was diluted with DMSO to prepare solution I at a concentration of 1600 μM. Then a certain volume of the 1600 μM solution I was diluted with 45% methanol to prepare working solution II at a concentration of 16 μM. The 30 mM stock solution and the 1600 μM solution II for the compound of formula I were also prepared by the above method.
1.4 Sample Incubation
5 μL of the 16 μM working solution of the compound of Example 5 was added to 75 μL plasma at a final concentration of 1 μM. The samples were incubated in a 37° C. water bath for 0, 15, 30, 60, 90, 120 and 180 min. After completion of the incubation, 240 μL of internal standard containing acetonitrile was added into the samples which was then shaken on a shaker at 800 rpm for 10 min and centrifuged at 3700 rpm at 4° C. for 20 min. The supernatant was analyzed by LC-MS, and the injection volume was 2 μL.
1.5 Preparation of Standard Curve
The previously 1600 μM solution I was diluted with acetonitrile to prepare the standard curve working solution with concentrations of 160, 400, 1600, 4000, 8000, 16000 and 32000 ng/mL. The concentration of QC working solution was 480, 1920 and 25600 ng/mL. 5 μL of the standard curve working solution and QC working solution were added to 75 μL plasma to obtain the standard curve samples with final concentrations of 10, 25, 100, 250, 500, 1000 and 2000 ng/mL and QC samples with final concentrations of 30, 120 and 1600 ng/mL. 240 μL of acetocyano containing the internal standard was then added into the samples quickly, which was then shaken in a shaker at 800 rpm for 10 min and centrifuged at 3700 rpm at 4° C. for 20 min. The supernatant was collected and analyzed by LC-MS, and the injection volume was 2 μL.
The standard curve of the compound of formula I and QC sample were prepared by the above method.

2. Results
The conversion of the compound of Example 5 of the present invention in fresh human plasma is as follows, and the data are shown in Table 2:

TABLE 2

| Time point (min) | Compound of Example 5 (μM) | Compound of formula 1 (μM) |
|---|---|---|
| 0 | 1 | 0.00 |
| 15 | 0.53 | 0.78 |
| 30 | 0.12 | 1.18 |
| 60 | 0.01 | 1.22 |
| 90 | 0.00 | 1.31 |
| 120 | 0.00 | 1.28 |
| 180 | 0.00 | 1.02 |

Conclusion: the compound was completely converted into the compound of formula I in human fresh plasma in about 30 min.

Test Example 3: Plasma Stability Test 1.1 Test Drug
The compounds of Example 4, Example 6, Example 10 and Example 11.
1.2 Test Plasma
Human fresh plasma was donated by volunteers with informed consent.
1.3 Experimental Steps
1) The test compounds in Table 3 were respectively prepared into 30 mM stock solutions with DMSO for later use.
2) The 30 mM stock solution was diluted with DMSO solution to solution I at a concentration of 1600 μM. Then the 1600 μM solution I was diluted with acetonitrile (ACN) to a working solution II at a concentration of 16 μM.
3) 7 time points of 0, 15, 30, 60, 90, 120 and 180 min were set in the experiment with two parallel samples for each time point. Two sample groups were set for each compound. 75 μL plasma and 5 μL of the above prepared working solution II with a concentration of 16 μM were added to each group. The reaction system was incubated at 37° C. until the preset time when the reaction was stopped by 300 μL of the ACN solution containing the internal standard. The reaction mixture was centrifuged at 3700 rpm for 10 min, and the supernatant was collected for analysis.
4) Preparation of the standard curve: the previously diluted 1600 μM solution I was diluted with acetonitrile to 1.5 μM/mL solution III as the standard curve for later use. The standard curve concentration was set to 0.32, 0.8, 1.6, 4.0, 8, 12, 16 and 42 uM. After dilution of each concentration of the standard curve, 75 μL plasma was added to 5 μL of each concentration point at a final concentration of 0.02, 0.05, 0.1, 0.25, 0.75, 1.0 and 1.5 uM, respectively. 300 μL stop solution was then added to the samples quickly which was then centrifuged at 3700 rpm for 10 min, and the supernatant was collected for LC-MSMS analysis. The data are shown in Table 3.

TABLE 3

| Time point (min) | Example 4 μM$^a$ | Example 4 μM$^b$ | Example 6 μM$^a$ | Example 6 μM$^b$ | Example 10 μM$^a$ | Example 10 μM$^b$ | Example 11 μM$^a$ | Example 11 μM$^b$ |
|---|---|---|---|---|---|---|---|---|
| 0 | 1.16 | 0 | 0.98 | 0.01 | 1.04 | 0.00 | 1.01 | 0.01 |
| 15 | 0.98 | 0 | 0.85 | 0.01 | 0.92 | 0.00 | 0.99 | 0.00 |

TABLE 3-continued

| Time point (min) | Example 4 μM[a] | Example 4 μM[b] | Example 6 μM[a] | Example 6 μM[b] | Example 10 μM[a] | Example 10 μM[b] | Example 11 μM[a] | Example 11 μM[b] |
|---|---|---|---|---|---|---|---|---|
| 30 | 0.99 | 0 | 0.91 | 0.01 | 0.97 | 0.00 | 0.91 | 0.00 |
| 60 | 1.00 | 0 | 0.85 | 0.01 | 0.96 | 0.00 | 0.92 | 0.01 |
| 90 | 0.97 | 0 | 0.77 | 0.01 | 0.93 | 0.00 | 1.03 | 0.00 |
| 120 | 0.81 | 0 | 0.70 | 0.01 | 0.95 | 0.00 | 0.97 | 0.00 |
| 180 | 0.78 | 0 | 0.53 | 0.01 | 0.88 | 0.00 | 0.95 | 0.00 |

Note:
[a] the plasma concentration of the compound of the examples, [b] the plasma concentration of rolapitant after metabolism of the compound of the examples.

Conclusion: The compounds in Example 4, Example 10 and Example 11 are relatively stable in plasma with relatively longer half-life in plasma, but only a small portion of these three compounds are metabolized to rolapitant in plasma. The compound in Example 6 can be metabolized to rolapitant in plasma, but it can be seen from the above data that the overall amount of metabolism in plasma is relatively small.

Test Example 4

The metabolism of the compounds of Example 1, Example 2 and Example 8 in the plasma of mouse, rat and human was determined by referring to the test method in Test Example 2. The data are shown in Table 4.

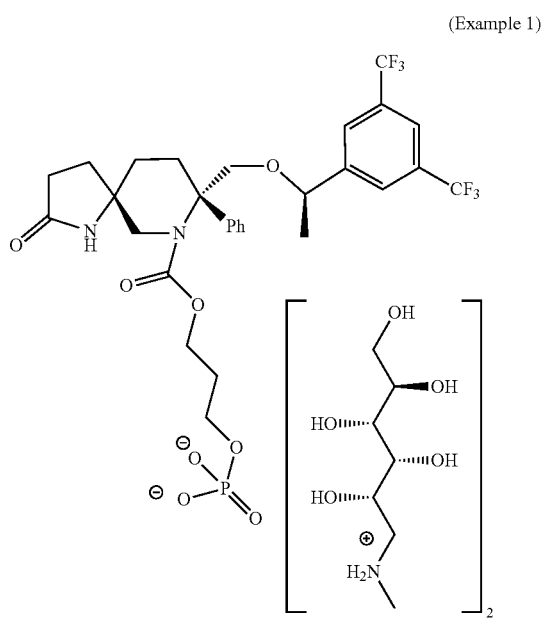
(Example 1)

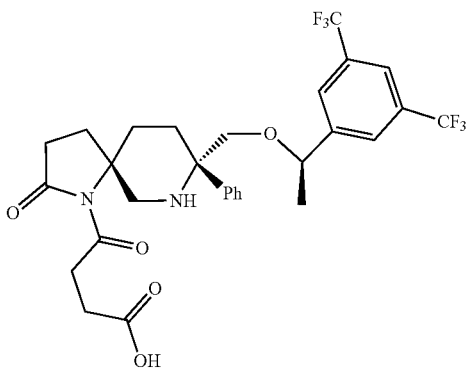
(Example 8)

TABLE 4

| | Example 1 μM[a] | Example 1 μM[b] | Example 2 μM[a] | Example 2 μM[b] | Example 8 μM[a] | Example 8 μM[b] |
|---|---|---|---|---|---|---|
| Mouse | 72.84 | 27.16 | 91.17 | 8.83 | 61.67 | 38.33 |
| Rat | 62.04 | 37.96 | 97.70 | 2.30 | 59.89 | 40.11 |
| Human plasma | 93.47 | 6.53 | 99.00 | 1.00 | 54.54 | 45.46 |

Note:
[a] the plasma concentration of the compounds of the examples, [b] the plasma concentration of rolapitant after metabolism of the compounds of the examples.

Conclusions: The compound of Example 8 can be converted into rolapitant in the plasma of mouse, rat and human, notably, the conversion rate in human plasma is nearly 46%. Meanwhile, the compounds of Example 1 and Example 2 had basically no convertion into rolapitant in human plasma, or only a slight conversion.

Test Example 5: In Vivo Pharmacokinetic Test in Rats

Rats were used as the test animals. The plasma drug concentration at different time points after administration of the compounds of Example 1 and Example 2 by injection was determined using LC/MS/MS method. The in vivo pharmacokinetic of the compounds in rats was studied, and the pharmacokinetic characteristics were evaluated.
Preparation of Drug
A certain amount of the compounds of Example 1 and Example 2 were weighed and prepared into a pH=4.0 solution by using 20 mmol/L sodium dihydrogen phosphate for later use.
1.1 Drug Administration
The drug was administered by intravenous bolus injection with an injection time of about 5 min, administration dose of 2 mg/kg, administration concentration of 0.4 mg/ml and administration volume of 5 ml/kg.
1.2 Operation
Blood was collected from the orbital vein before administration and 5 min, 0.25 h, 0.5 h, 1 h, 2 h, 4 h, 6 h, 8 h, 10 h, 24 h and 48 h after administration. About 0.6 mL was collected for each sample which was subject to anticoagulation using heparin sodium and placed on ice immediately after collection. The blood samples were placed in labeled centrifuge tubes after collection, and plasma was separated by centrifugation (centrifugation conditions: centrifugal force 2200 g, centrifugation at 2-8° C. for 10 min).

1.3 Results of Pharmacokinetic Parameters

TABLE 5

|  | Compound of Example 1 | | Compound of Example 2 | |
| --- | --- | --- | --- | --- |
|  | (ng/ml)[a] | (ng/ml)[b] | (ng/ml)[a] | (ng/ml)[b] |
| $AUC_{0-t}$ (ng/mL *h) | 1076 | 3638 | 41.6 | 1834 |
| $AUC_{0-\infty}$ (ng/mL * h) | 1081 | 27738 | 42.2 | 796 |
| $T_{1/2}$(h) | 0.297 | 81.4 | 0.087 | 4.80 |
| MRT 0-∞ (h) | 0.092 | 118 | 0.073 | 7.68 |

Note:
[a] the in vivo pharmacokinetic parameters of the compounds of the examples in rat,
[b] the in vivo pharmacokinetic parameters of rolapitant after metabolism of the compounds of examples in rat.

Conclusions: Although the compound of Example 1 is basically not metabolized in vitro, especially in human plasma, to the active substance rolapitant, it shows excellent pharmacokinetic data of rolapitant in rats, which indicates that the compound of Example 1 has been metabolized to rolapitant in vivo. Moreover, from the data of $AUC_{0-\infty}$, $AUC_{0-t}$ and $T_{1/2}$, the in vivo metabolic cycle of compound 1 after administration is longer, and the absorption and exposure level of compound 1 are comparable to that of rolapitant.

Test Example 6: Pharmacokinetic Test of the Compounds in Cynomolgus Monkeys

Cynomolgus monkeys were used as the test animals. The plasma drug concentration at different time points after iv administration of the compound of Example 5 by injection was determined using LC/MS/MS method. The in vivo pharmacokinetic of the compound of the present invention in cynomolgus monkeys was studied, and the pharmacokinetic characteristics were evaluated.
Preparation of Drug
A certain amount of the compound of Example 5 was weighed and prepared into a pH=4.0 solution by using 20 mmol/L sodium dihydrogen phosphate for later use.
1.1 Drug Administration
The drug was administered by intravenous with injection time of about 30 min, administration dose of 2 mg/kg, administration concentration of 0.4 mg/ml and administration volume of 5 ml/kg.
1.2 Operation
Blood was collected from the femoral vein before administration and 5 min, 0.25 h, 0.5 h, 1 h, 2 h, 4 h, 6 h, 8 h, 10 h, 24 h and 48 h after administration. About 0.6 ml of was collected for each sample, which was subject to anticoagulation using heparin sodium and placed on ice immediately after collection. The blood samples were placed in labeled centrifuge tubes after collection, and plasma was separated by centrifugation (centrifugation conditions: centrifugal force 2200 g, centrifugation at 2-8° C. for 10 min).
The content of the compound of Example 5 and rolapitant in plasma samples was determined by LC/MS/MS.
1.3 Results of Pharmacokinetic Parameters

TABLE 6

| Compound | Compound of Example 5 | Rolapitant (compound of formula I) |
| --- | --- | --- |
| Tmax (h) | 0.11 ± 0.12 | 0.14 ± 0.10 |
| Cmax (ng/mL) | 2.28 ± 0.39 | 315.25 ± 97.08 |
| $AUC_{0-t}$ (ng/mL * h) | 0.77 ± 0.29 | 4326.87 ± 1820.65 |

Conclusions: In the pharmacokinetic study of the compound of Example 5 in cynomolgus monkeys, most of the compound were rapidly transformed into the active metabolite rolapitant in cynomolgus monkeys, which has good pharmacokinetic properties.

Example 19

Compound 3 was prepared by referring to steps 1-2 in Example 1. Then compound 3 (6.65 g, 8.67 mmol, 1 eq) was dissolved in dichloromethane (200 mL) in a 500 mL single-necked flask under $N_2$ atmosphere, and trifluoroacetic acid (9.89 g, 86.7 mmol, 10.0 eq) was added slowly under cooling in ice water. The reaction mixture was stirred until completion of the reaction. The reaction mixture was concentrated to give 2.29 g oil, which was purified by reversed-phase silica gel column (C18) (A solution: 20 mmol aqueous solution of $NH_4HCO_3$, B solution: acetonitrile) and then adjusted to pH=1~2 with 1 M phosphoric acid, extracted with dichloromethane, washed with saturated brine, dried over anhydrous sodium sulfate, filtered and concentrated to give 2.7 g of the target product.

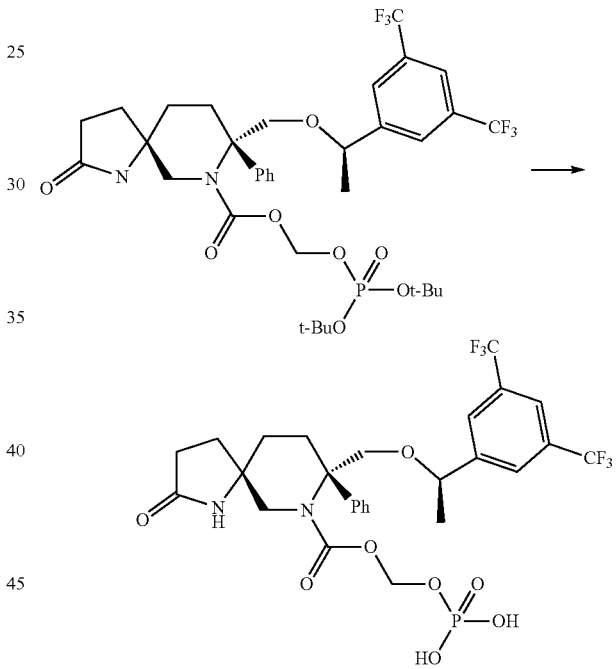

Test Example 7: Solubility

Solubility of the compound of Example 19 at different pH values were measured by referring to the solubility test method of Test Example 1. The data are as follows:

TABLE 7

| pH | Solubility | Saturation solubility |
| --- | --- | --- |
| 7.4 | 26 mg/ml | 19.8 mg/ml |
| 9.0 | 28 mg/ml | 21.4 mg/ml |

Test Example 8: Hemolytic Effect

Red blood cells (RBC) were collected from the jugular vein or central ear artery of rabbits (10 ml of EDTA whole blood). The blood was put in a conical flask with glass beads and shaken for 10 minutes to remove fibrinogen, resulting in defibrinated blood. About 10 times the amount of sodium chloride solution was added to the defibrinated blood, which was then shaken well and centrifuged at 1500 rpm for 10 minutes. The supernatant was removed and the precipitated red blood cells were washed with sodium chloride injection for 3 times according to the above method, until the supernatant was observed colorless. The obtained red blood cells were prepared into a 2% (v/v) suspension with sodium chloride injection for later use.

The test samples (the compound of Example 5 and the compound of Example 19) were respectively dissolved in PBS (pH 7.4 or pH 5) and filtered to prepare 0.4 mg/ml, 0.8 mg/ml, 1.2 mg/ml, 1.6 mg/ml and 2 mg/ml solutions for later use.

A certain amount of test sample solution was added to the above hemoglobin for testing in the supernatant.

If the solution in the test tube is clear and red, and there are no remaining cells or a small amount of remaining red blood cells at the bottom of the tube, it indicates that hemolysis has occurred. If all the red blood cells sink and the supernatant liquid is colorless and clear, it indicates that no hemolysis has occurred. If there are brown-red or red-brown flocculent precipitates in the solution, and still do not disperse after gently inverting for 3-5 times, it indicates that coagulation of red blood cell may occur. The sample should be further observed under a microscope, and if red blood cells can be seen as aggregated, then coagulation has occurred. The hemolytic effect of the compounds of the present disclosure was determined by using this method.

Conclusion: The compound of Example 19 has no hemolytic effect at a concentration up to 2 mg/ml, and the compound of Example 5 has hemolytic effect at a concentration of 0.04 mg/ml and higher.

Test Example 9: Hemolytic Effect of Rolapitant Emulsion

Rolapitant emulsion was prepared by referring to the method in CN102573475 (formula: 4.4% polyethylene glycol-15 hydroxystearate, 1.1% medium chain triglyceride and 0.66% soybean oil), and prepared into 0.18 mg/ml, 0.09 mg/ml, 0.045 mg/ml, 0.023 mg/ml, 0.011 mg/ml, 0.056 mg/ml and 0.028 mg/ml with PBS for later use.

Hemolytic effect was determined by referring to the method in Test Example 8.

Conclusion: rolapitant emulsions at all concentrations showed hemolytic effect.

Test Example 10: Pharmacokinetic Test in Cynomolgus Monkeys

Cynomolgus monkeys were used as the test animals. The plasma drug concentration at different times after administration of the compound prepared by referring to Example 19 by injection was determined by using the LC/MS/MS method. The in vivo pharmacokinetics of the compounds of the present invention in cynomolgus monkeys was studied, and the pharmacokinetic characteristics were evaluated.

Preparation of Drug

A certain amount of the test compound was weighed and prepared into a pH=4.0 solution by using 20 mmol/L sodium dihydrogen phosphate for later use.

1.1 Drug Administration

The drug was administered by intravenous drip with injection time of about 30 min, administration dose of 3.54 mg/kg, administration concentration of 2 mg/ml and administration volume of 5 ml/kg.

1.2 Operation

Blood was collected from the femoral vein before administration and 5 min, 0.25 h, 0.5 h, 1 h, 2 h, 4 h, 6 h, 8 h, 10 h and 24 h after administration. About 0.6 mL was collected for each sample, which was subject to anticoagulation using heparin sodium and placed on ice immediately after collection. The blood samples were placed in labeled centrifuge tubes after collection, and plasma was separated by centrifugation (centrifugation conditions: centrifugal force 2200 g, centrifugation at 2-8° C. for 10 min).

The content of the compound of Example 24 and rolapitant in plasma samples was determined by LC/MS/MS.

1.3 Results of Pharmacokinetic Parameters

TABLE 8

|  | Compounds | |
| --- | --- | --- |
|  | (ng/ml)[a] | (ng/ml)[b] |
| $AUC_{0-24\,h}$ (ng/mL * h) | 1434.78 | 8410.94 |
| $T_{1/2}(h)$ | 0.47 | 13.16 |
| MRT 0-∞ (h) | 0.26 | 8.17 |

Note:
[a]the in vivo pharmacokinetic parameters of the compounds of the examples in cynomolgus monkey,
[b]the in vivo pharmacokinetic parameters of rolapitant after metabolism of the compounds of the examples in cynomolgus monkey.

Conclusion: in the in vivo pharmacokinetic study of the compound in cynomolgus monkeys, most of the compound is rapidly converted to the active metabolite rolapitant in cynomolgus monkeys, and the compound has good pharmacokinetic properties. In addition, compared with the compound of Example 5, the compound has a higher in vivo bioavailability in cynomolgus monkeys.

What is claimed is:

1. A compound of formula (III):

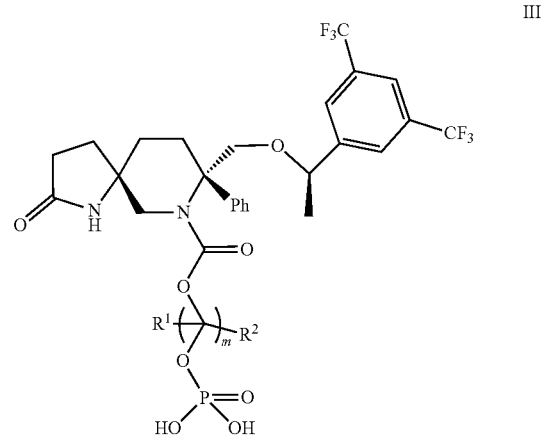

or a pharmaceutically acceptable salt thereof, or a stereoisomer, rotamer or tautomer thereof, wherein, m=1, 2, 3 or 4; $R^1$ and $R^2$ are each independently selected from the group consisting of hydrogen, alkyl, cycloalkyl, heterocyclyl, aryl and heteroaryl, said alkyl, cycloalkyl, heterocyclyl, aryl or heteroaryl is optionally substituted with one or more groups selected from the group consisting of alkyl, cycloalkyl, alkoxyl, hydroxyalkyl, alkenyl, alkynyl, aryl, heteroaryl, nitro, cyano, hydroxyl, halogen, SR', NR'(R''), COOR' and CONR'(R''); R' and R'' are each independently selected from the group consisting of hydrogen, hydroxyl, alkyl, alkoxyl, alkenyl and acyl.

2. The compound according to claim 1, wherein the compound of formula (III) is selected from the group consisting of:

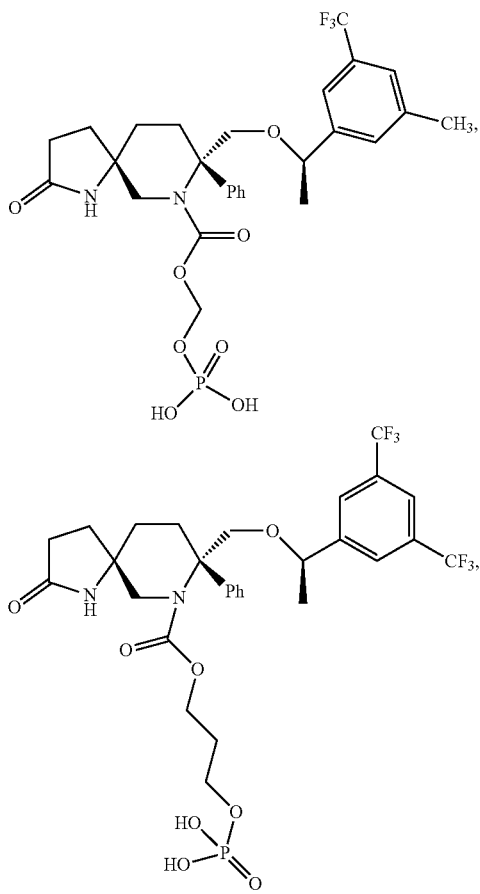

or a pharmaceutically acceptable salt thereof, a stereoisomer, rotamer or tautomer thereof, or a deuteride thereof.

3. A pharmaceutical composition comprising a therapeutically effective amount of the compound of claim 1, wherein the pharmaceutical composition comprises a pharmaceutically acceptable carrier, diluent or excipient.

4. A method of treating a physiological disorder, condition, or disease in a subject in need thereof, the method comprising administering to said subject, the compound according to claim 1.

5. The method of claim 4, wherein the physiological disorder, condition or disease is selected from the group consisting of asthma, vomiting, nausea, depression, anxiety, cough and migraine.

6. The method of claim 4, wherein the physiological disorder, condition or disease is a respiratory disease, cough, inflammatory disease, skin disorder, ophthalmological disorder, depression, anxiety, phobias, bipolar disorder, alcohol dependence, substance abuse with significant effect on nerves, epilepsy, nociception, psychosis, schizophrenia, Alzheimer's disease, AIDs-related dementia, Towne's disease, stress-related disorder, obsessive/compulsive disorder, bulemia, anorexia nervosa, binge eating, mania, premenstrual syndrome, gastrointestinal dysfunction, atherosclerosis, fibrotic disorder, obesity, type II diabetes, headache, neuropathic pain, post-action pain, chronic pain syndrome, bladder disorder, genitourinary disorder or vomiting or nausea.

7. The compound according to claim 1, wherein $R^1$ and $R^2$ are each independently selected from the group consisting of hydrogen, $C_{1-6}$ alkyl and $C_{3-7}$ cycloalkyl.

* * * * *